(12) United States Patent
Nearman et al.

(10) Patent No.: US 9,167,962 B2
(45) Date of Patent: Oct. 27, 2015

(54) AIRWAY MANAGEMENT

(71) Applicants: Howard S. Nearman, Pepper Pike, OH (US); Donald M. Voltz, Twinsburg, OH (US); Alon S. Aharon, Spokane, WA (US)

(72) Inventors: Howard S. Nearman, Pepper Pike, OH (US); Donald M. Voltz, Twinsburg, OH (US); Alon S. Aharon, Spokane, WA (US)

(73) Assignees: University Hospitals of Cleveland, Cleveland, OH (US); Amin, Turocy & Watson, LLP, Cleveland, OH (US)

( * ) Notice: Subject to any disclaimer, the term of this patent is extended or adjusted under 35 U.S.C. 154(b) by 0 days.

(21) Appl. No.: 13/840,165

(22) Filed: Mar. 15, 2013

(65) Prior Publication Data

US 2013/0253274 A1    Sep. 26, 2013

Related U.S. Application Data

(63) Continuation of application No. 12/754,362, filed on Apr. 5, 2010, now Pat. No. 8,419,634, which is a continuation-in-part of application No. 12/636,271, filed on Dec. 11, 2009, now Pat. No. 8,460,184.

(51) Int. Cl.
*A61B 1/267* (2006.01)
*A61B 1/00* (2006.01)
*A61B 1/008* (2006.01)

(52) U.S. Cl.
CPC ............. *A61B 1/267* (2013.01); *A61B 1/008* (2013.01); *A61B 1/00041* (2013.01); *A61B 1/2673* (2013.01)

(58) Field of Classification Search
CPC ............ A61B 1/267; A61B 1/00052; A61B 1/00105; A61B 1/04; A61B 1/06; A61B 1/0684; A61B 1/2673; A61B 1/0676; A61B 1/00045; A61B 1/227; A61B 1/00103; A61B 1/05; A61B 1/0008; A61B 1/00135

USPC .................................................. 600/188-199
See application file for complete search history.

(56) References Cited

U.S. PATENT DOCUMENTS 3,913,568 A    10/1975  Carpenter
4,126,127 A    11/1978  May
(Continued)

FOREIGN PATENT DOCUMENTS

DE    29921801 U    3/2000
EP    1285623 A1    2/2003
(Continued)

OTHER PUBLICATIONS

Chinese Office Action dated Feb. 28, 2013 for CN Application No. 200880103408.4, 8 pages.
(Continued)

*Primary Examiner* — Mary Hoffman
*Assistant Examiner* — Tara R Carter
(74) *Attorney, Agent, or Firm* — Amin, Turocy & Watson, LLP

(57) ABSTRACT

The claimed subject matter provides systems and/or methods that facilitate improving visualization associated with intubation. A dynamical articulating laryngoscope can include a handle assembly and a blade assembly. The blade assembly can further include a main blade assembly, a proximal blade assembly, and a distal blade assembly. A medium control articulation point can couple the main blade assembly and the proximal blade assembly, and a fine control articulation point can couple the distal blade assembly and the proximal blade assembly. Further, the proximal blade assembly can pivot relative to the main blade assembly around the medium control articulation point and/or the distal blade assembly can pivot relative to the proximal blade assembly around the fine control articulation point. Pivoting about the medium control articulation point and/or the fine control articulation point can be effectuated by one or more blade control components.

20 Claims, 22 Drawing Sheets

(56) References Cited

U.S. PATENT DOCUMENTS

| | | | |
|---|---|---|---|
| 4,337,761 | A | 7/1982 | Upsher |
| 4,384,570 | A | 5/1983 | Roberts |
| 4,573,451 | A | 3/1986 | Bauman |
| 5,840,013 | A | 11/1998 | Lee |
| 6,042,542 | A * | 3/2000 | Koros et al. ............ 600/231 |
| 6,053,166 | A | 4/2000 | Gomez |
| 6,543,447 | B2 | 4/2003 | Pacey |
| 6,655,377 | B2 | 12/2003 | Pacey |
| 6,843,769 | B1 | 1/2005 | Gandarias |
| 6,991,604 | B2 | 1/2006 | Cantrell |
| 7,089,928 | B2 | 8/2006 | Besharim et al. |
| 7,153,260 | B1 | 12/2006 | Girgis |
| 8,416,291 | B2 * | 4/2013 | Carrey et al. ............ 348/77 |
| 2002/0022769 | A1 * | 2/2002 | Smith et al. ............ 600/188 |
| 2004/0215061 | A1 | 10/2004 | Kimmel et al. |
| 2006/0020171 | A1 | 1/2006 | Gilreath |
| 2006/0122475 | A1 | 6/2006 | Balberg et al. |
| 2006/0221191 | A1 | 10/2006 | Nonaka et al. |
| 2007/0038023 | A1 | 2/2007 | Uchimura et al. |
| 2007/0129603 | A1 | 6/2007 | Hirsh |
| 2007/0179342 | A1 | 8/2007 | Miller et al. |
| 2009/0209826 | A1 * | 8/2009 | Sanders et al. ............ 600/188 |

FOREIGN PATENT DOCUMENTS

| | | |
|---|---|---|
| FR | 2821736 A1 | 9/2002 |
| JP | 2003-117000 | 4/2003 |
| JP | 2005-334462 | 12/2005 |
| JP | 2006-000282 | 1/2006 |
| JP | 2006-198031 | 8/2006 |
| JP | 2007503931 | 3/2007 |
| KR | 1019990087101 | 12/1999 |
| WO | 93/11700 | 6/1993 |
| WO | 97/30626 | 8/1997 |
| WO | 02/11608 | 2/2002 |
| WO | 04/000107 | 12/2003 |

OTHER PUBLICATIONS

European Office Action for European Patent Application No. 08770700.6-2319 dated Dec. 4, 2012, 4 pages.
OA dated Oct. 26, 2012 for U.S. Appl. No. 12/636,271, 29 pages.
International Search Report dated Nov. 22, 2008 for PCT Application No. PCT/US08/66544, 13 pages.
EP Search Report for European Application No. 08770700.6-2319/2155040 dated Jun. 7, 2010, 7 pages.
Australian Office Action for Australian application No. 2008-266236, dated Nov. 8, 2010, 2 pages.
Korean OA dated Mar. 31, 2011 for Korean Patent Application No. 10-2010-7000584, 7 pages.
CN OA dated Sep. 21, 2011 for Chinese Application No. 200880103408.4, 9 pages.
Australian Office Action dated Nov. 30, 2011 for for Australian application No. 2008-266236, 3 pages.
Japanese OA dated Nov. 21, 2011 for JP Application No. 2010-512319, 3 pages.
EP OA dated Dec. 16, 2011 for European Application No. 08770700.6, 6 pages.
Canadian OA dated Mar. 21, 2012 for Canadian Patent Application No. 2689676, 3 pages.
OA mailed Jun. 19, 2012 for U.S. Appl. No. 12/754,362, 30 pages.
OA dated May 10, 2012 for U.S. Appl. No. 12/636,271, 34 pages.
CN OA dated Jul. 31, 2012 for Chinese Application No. 200880103408.4, 10 pages.
Japanese OA, mailing date Jul. 31, 2012 for JP Application No. 2010-512319, 3 pages.
Israel OA dated Jun. 25, 2012 for Israel Patent Application No. 202541, 5 pages.
Office Action dated Jun. 26, 2014 for U.S. Appl. No. 13/914,472, 24 pages.
Final Office action dated Oct. 7, 2014 for U.S. Appl. No. 13/914,472, 12 pages.
Non-Final Office Action dated Jan. 27, 2015 for U.S. Appl. No. 13/914,472, 19 pages.

* cited by examiner

AIRWAY MANAGEMENT

CROSS-REFERENCE TO RELATED APPLICATIONS

This application is a continuation of U.S. patent application Ser. No. 12/754,362, filed Apr. 5, 2010, and entitled "APPARATUS AND METHOD FOR AIRWAY MANAGEMENT", which is a continuation-in-part of U.S. patent application Ser. No. 12/636,271, filed Dec. 11, 2009, and entitled "AIRWAY MANAGEMENT", which is a U.S. National Stage Filing of Patent Cooperation Treaty (PCT) Application Serial No. PCT/US08/66544, filed Jun. 11, 2008, and entitled "AIRWAY MANAGEMENT", which claims the benefit of U.S. Provisional Patent Application Ser. No. 60/943,320, filed Jun. 12, 2007, and entitled "AIRWAY MANAGEMENT". The entireties of the aforementioned applications are expressly incorporated herein by reference.

BACKGROUND

Medical endoscopy has continued to advance with increasing sophistication in both camera and illumination technology. The area of airway management has also embraced technological advances in optics and light transmission resulting in development of numerous devices to assist a medical provider with placement of a breathing tube into the trachea of a patient requiring mechanical ventilatory assistance (e.g., endotracheal intubation).

An area of airway management which has not seen much advancement since the introduction of peroral endotracheal intubation in the 18th century is the design of the laryngoscopic instrument used to displace the tongue and allow for visualization of vocal cords and laryngeal aperture. A number of subtle changes have been implemented in these tools resulting in many different variations in the laryngoscopic blade. These devices, although quite varied in design, are placed into the oral cavity and used to forcefully move the tongue, mandible, and connected soft tissue out of the way allowing for visualization of the tracheal inlet. This maneuver can be highly stimulating to patients necessitating some form of anesthesia to tolerate its use. In addition, even with increasing levels of force applied to the device, there are patients with anatomical variants or pathologic conditions that do not allow direct visualization of the tracheal opening.

In the United States, it has been estimated that 10 million people undergo general anesthesia each year for a variety of operations. During the induction of general anesthesia, a significant percentage of patients require placement of an endotracheal tube along with mechanical ventilation to overcome cessation of breathing caused by anesthetic medications. The process of placing an endotracheal tube into the trachea varies in difficulty depending on a patient's body habitus, variations in normal anatomy, as well as variations in anatomic deviations as a result of numerous pathologic processes. Placement of the endotracheal tube depends both on the skills of the anesthesiologist as well as the instruments used to visualize the opening of the trachea. In a normal anesthetic situation, once a patient is placed under general anesthesia, a rigid laryngoscope can be placed into the mouth to displace the tongue allowing for exposure of the laryngeal aperture. Once the larynx is visualized, an endotracheal tube can be placed into the trachea and a high volume, low pressure cuff can be inflated to provide a seal between the endotracheal tube and the inner wall of the trachea. Numerous risks and complications can occur with the placement of an endotracheal tube, risks that increase in patients with abnormal body habitus (such as morbid obesity), or variations in normal anatomy as the result of congenital or pathologic conditions. Thus, anesthesiologists desire to quickly, reliably and safely place an endotracheal tube after anesthetic induction to mitigate chances of the patient becoming hypoxic (e.g., lack of oxygen in the blood) resulting in injury to systems in the body, especially the heart and the brain. For example, it has been estimated that intubation problems account for about one third of all deaths and serious injuries related to anesthesiology. In addition, many more patients are placed at risk outside the operating room. For instance, emergent placement of an endotracheal tube can be encountered when a patient experiences cardiac and/or respiratory arrest, both inside and outside the hospital setting. A challenge for anesthesiologists as well as other health care providers who have specialty training in the area of airway management is to place the endotracheal tube in a position far removed from where they are visualizing it (e.g., viewing from the mouth opening for traditional laryngoscopy).

SUMMARY

The following presents a simplified summary in order to provide a basic understanding of some aspects described herein. This summary is not an extensive overview of the claimed subject matter. It is intended to neither identify key or critical elements of the claimed subject matter nor delineate the scope thereof. Its sole purpose is to present some concepts in a simplified form as a prelude to the more detailed description that is presented later.

The claimed subject matter relates to systems and/or methods that facilitate improving visualization associated with intubation. A dynamically articulating laryngoscope blade can be controlled to configure to normal anatomic variants and pathological abnormalities to facilitate placing of an endotracheal tube into a patient's trachea. Further, cameras can be integrated into and/or mounted upon the dynamically articulating laryngoscope blade. The cameras can enable stereoscopic visualization of the laryngeal aperture allowing for depth perception. Moreover, the cameras can be moved independently of the blade allowing for optimal viewing of the laryngeal opening.

Manipulation of patient airway anatomy can provide for a clearer visualization of the laryngeal aperture, from which observations can be made and related data collected. In accordance with various aspects of the claimed subject matter, data observed from the oral cavity can be retained in a data store. For example, videos and/or images can be collected within the data store associated with an airway management apparatus (e.g., laryngoscope). Further, the videos and/or images can be archived when the apparatus is placed in a cradle (e.g., uploaded to a hospital server). Additionally or alternatively, the videos and/or images can be retained upon memory (e.g., flash) that can be removed from the apparatus (e.g., and included in a patient's file, used for training/documentation purposes, shared for collaborative diagnosis or research endeavors, . . . ). In another example, the dynamically articulating laryngoscope blade (or a handle associated therewith) can include a microphone, which can record sounds that can be retained in the data store; the sounds, for instance, can include an operator's voice which can be collected using the microphone to add notes corresponding to the videos and/or images.

Pursuant to one or more aspects of the claimed subject matter, collected data can be wirelessly transmitted to a disparate device for real time presentation. For example, the videos and/or images can be wireless transmitted from the apparatus to a disparate device capable of presenting a corresponding output. Therefore, while the laryngoscope is positioned within the oral cavity, feedback can be output to the user of the laryngoscope (and/or any disparate user). It is contemplated that any type of wireless communication technology can be leveraged to communicate the collected data to the disparate device. Further, control of the articulating blade and/or cameras can be obtained from the disparate device via the wireless communication.

In accordance with various aspects of the claimed subject matter, a dynamical articulating laryngoscope can include a handle assembly and a blade assembly. The blade assembly can further include a main blade assembly, a proximal blade assembly, and a distal blade assembly. A medium control articulation point can couple the main blade assembly and the proximal blade assembly, and a fine control articulation point can couple the distal blade assembly and the proximal blade assembly. Further, the proximal blade assembly can pivot relative to the main blade assembly around the medium control articulation point and/or the distal blade assembly can pivot relative to the proximal blade assembly around the fine control articulation point. Pivoting about the medium control articulation point and/or the fine control articulation point can be effectuated by one or more blade control components.

The following description and the annexed drawings set forth in detail certain illustrative aspects of the claimed subject matter. These aspects are indicative, however, of but a few of the various ways in which the principles of such matter may be employed and the claimed subject matter is intended to include all such aspects and their equivalents. Other advantages and novel features will become apparent from the following detailed description when considered in conjunction with the drawings.

DETAILED DESCRIPTION

Figure 1:
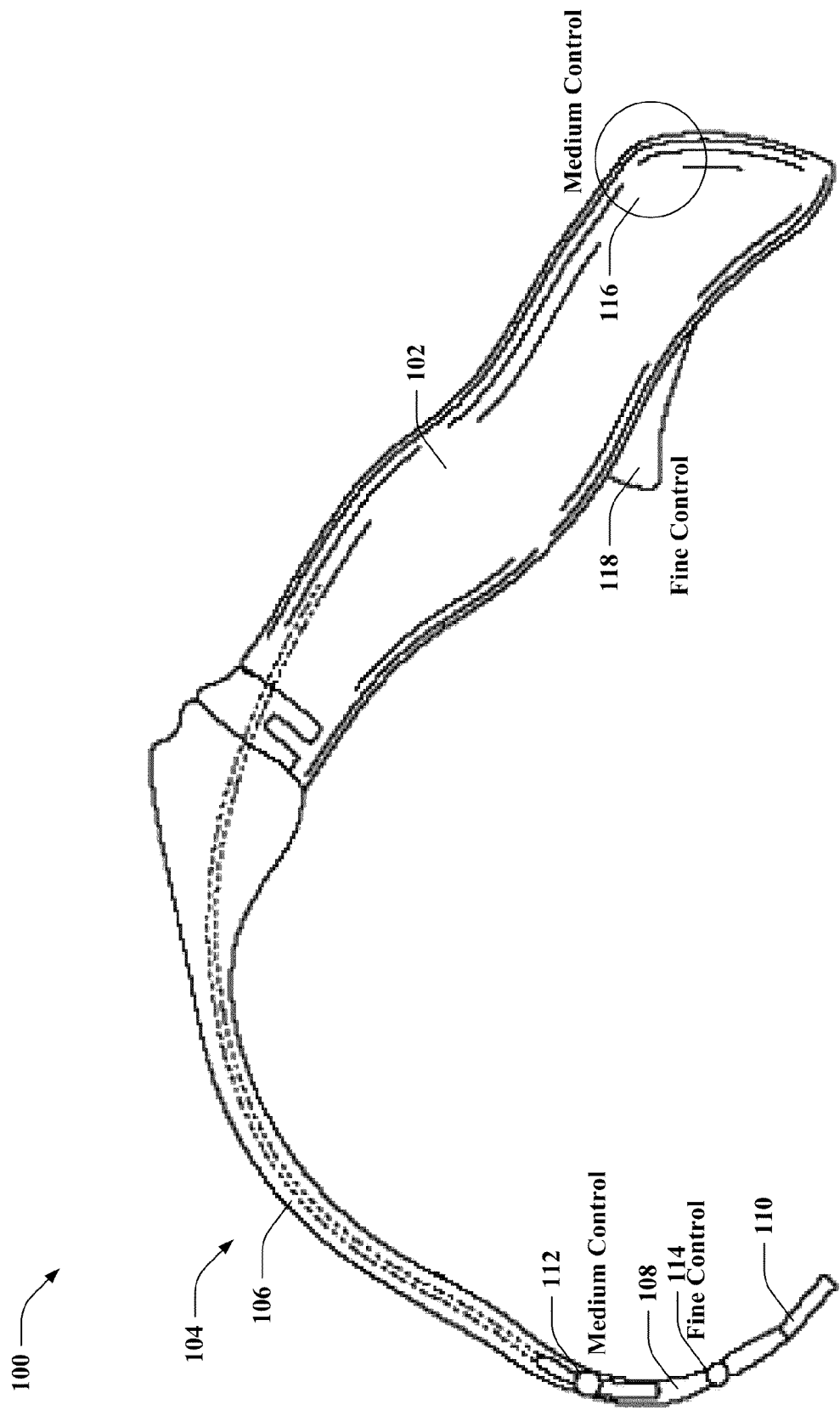
FIG. 1 illustrates an example schematic of an airway management apparatus in accordance with various aspects of the claimed subject matter.

The claimed subject matter is described with reference to the drawings, wherein like reference numerals are used to refer to like elements throughout. In the following description, for purposes of explanation, numerous specific details are set forth in order to provide a thorough understanding of the subject innovation. It may be evident, however, that the claimed subject matter may be practiced without these specific details. In other instances, well-known structures and devices are shown in block diagram form in order to facilitate describing the subject innovation.

As utilized herein, terms "component," "system," and the like are intended to refer to a computer-related entity, either hardware, software (e.g., in execution), and/or firmware. For example, a component can be a process running on a processor, a processor, an object, an executable, a program, and/or a computer. By way of illustration, both an application running on a server and the server can be a component. One or more components can reside within a process and a component can be localized on one computer and/or distributed between two or more computers.

Furthermore, the claimed subject matter may be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, carrier, or media. For example, computer readable media can include but are not limited to magnetic storage devices (e.g., hard disk, floppy disk, magnetic strips, . . . ), optical disks (e.g., compact disk (CD), digital versatile disk (DVD), . . . ), smart cards, and flash memory devices (e.g., card, stick, key drive, . . . ). Additionally it should be appreciated that a carrier wave can be employed to carry computer-readable electronic data such as those used in transmitting and receiving electronic mail or in accessing a network such as the Internet or a local area network (LAN). Of course, those skilled in the art will recognize many modifications may be made to this configuration without departing from the scope or spirit of the claimed subject matter. Moreover, the word "exemplary" is used herein to mean serving as an example, instance, or illustration. Any aspect or design described herein as "exemplary" is not necessarily to be construed as preferred or advantageous over other aspects or designs.

Now turning to the figures, FIG. 1 illustrates an example schematic of an airway management apparatus 100 in accordance with various aspects of the claimed subject matter. It is to be appreciated that the claimed subject matter is not limited to the depicted example schematic. The airway management apparatus 100 can enable placement of an endotracheal tube during induction of general anesthesia and/or for emergency management of the airway during any type of respiratory embarrassment in a controlled operating room environment, other hospital location such as the emergency department, or outside the hospital in any number of field situations. For example, the airway management apparatus 100 can include one or more cameras that can be maneuvered in close proximity to the opening of the trachea. By allowing maneuvering of the one or more cameras, a health care provider employing the airway management apparatus 100 can have an increased chance of appropriately placing an endotracheal tube. Further, the airway management apparatus 100 can provide direct, visual feedback that the endotracheal tube is in a proper place, and thus, mitigate adverse events associated with a misplaced tube.

The airway management apparatus 100 can be a self-contained single piece. For instance, the airway management apparatus 100 can include a handle 102 and a blade 104. As such, the airway management apparatus 100 can have similarity to a conventional Macintosh laryngoscope with notable variations as discuss below. According to another example, the blade 104 can be removable from the handle 102 of the airway management apparatus 100 and/or replaceable (e.g., the blade 104 or a portion thereof can be disposable); however, the blade 104 need not be removable from the handle 102 and/or replaceable. It is contemplated that blades of various sizes, shapes, thicknesses, material compositions, etc. can be attached to a common handle, for instance. According to another illustration, it is to be appreciated that the handle 102 can be a universal handle; as such, the handle 102 can interchangeably connect with the blade 104 and/or any disparate type of device (e.g., bronchoscope, ENT Dido scope, . . . ) while providing similar functionality (e.g., power source, wireless communication, data storage, . . . ) as described below to each of these disparate types of devices. Such a universal handle 102 can be portable. Further, the universal handle 102 can include servo-control capabilities that can effectuate operating substantially any type of device to which the handle 102 is attached. Moreover, the universal handle 102 can enable acquisition, archiving, transmission (e.g., wireless, wired, . . . ), generation of reports, etc. related to data associated with the attached device (e.g., the blade 104, bronchoscope, ENT Dido scope, mediastinoscope, colonoscope, . . . ) as described below. For example, data can be obtained via the device attached to the universal handle 102 by way of fiberoptics, cameras, ultrasound, and/or substantially any type of sensor(s).

The blade 104 can be a dynamically articulating laryngoscope blade that can be controlled to configure to normal anatomic variants as well as pathologic abnormalities to facilitate placing an endotracheal tube into the trachea. Thus, the blade 104 can accommodate variation in normal and abnormal anatomy of the upper airway resulting in less airway trauma and stimulation stress on a patient undergoing intubation. In contrast to conventional blades that commonly have fixed curvature, the blade 104 can be controlled via the handle 102 to adjust the curvature, manipulate portions or the entire blade 104 relative to the handle 102, etc. Accordingly, the airway management apparatus 100 can be slid along the handle 102 to lengthen or shorten the blade. Further, upon obtaining the proper blade length, the blade 104 can be flexed up or down via a medium control to provide a crude view of the vocal cords (e.g., camera(s) can be positioned nearby the medium control articulation point). Additionally, a tip of the blade 104 can be manipulated via a fine control to alter the position of a patient's epiglottis to provide a clearer view of the vocal cords. It is contemplated that the blade 104 can be manipulated at any disparate location(s) upon the blade 104 other than or in addition to those depicted in the illustrated schematic.

The blade 104 can also have one or more digital cameras (e.g., stereoscopic cameras) mounted thereupon. The digital camera(s) can be moved independently of the blade 104, for instance, to allow for optimal viewing of the laryngeal opening. Further, articulation of the blade 104 can enable positioning the camera(s) such that an unobstructed view of the vocal cords can be obtained. It is to be appreciated that the camera(s) can be integrated into the blade 104, attached to the blade 104 (e.g., permanently, temporarily, . . . ), and so forth. According to an example, the camera(s) can be removeably connected to the blade 104 thereby allowing for replacement.

The handle 102 can include a power supply. For instance, the power supply can be a battery (e.g., a lithium-battery). Additionally, the handle 102 can comprise an interface that enables connecting to a cradle. When connected to (e.g., docked upon) the cradle, the power supply can be recharged, digital images and/or video obtained by the one or more digital cameras can be transferred, and so forth. In addition, the airway management apparatus 100 (e.g., the handle 102) can include an integrated processor. By way of illustration, the processor can control operation associated with the one or more digital cameras; thus, the processor can enable capturing digital images and/or video with the camera(s) and/or transferring the captured data to a remote location (e.g., via the interface when connected to the cradle, a wireless connection, . . . ).

The handle 102 can also include controls (e.g., a medium control component 116, a fine control component 118, . . . ) that allow for manipulation of the articulating blade 104. The differing controls can provide varying precision of manipulation (e.g., medium control, fine control, . . . ). By way of illustration, the controls included with the handle 102 can mechanically alter the size, shape, curvature, orientation, etc. of the blade 104. Additionally or alternatively, the controls can transmit a signal that can initiate such alterations (e.g., employing a servo motor). Also, the handle 102 can comprise a control that releases the integrated channel for passage of the endotracheal tube or other airway device.

The attached blade 104 can be constructed of a plurality of flat metal blades that articulate on one another allowing for the blade 104 to dynamically assume multiple configurations depending on the patient's airway anatomy. Thus, the blade 104 can include multiple articulating plates that allow the blade 104 to flex throughout its length as well as at the tip. The control apparatus for this manipulation can be positioned within the handle 102.

The airway management apparatus 100 can provide a number of advantages as compared to conventional devices. Every patient has a different anatomically structured airway and securing an airway can be difficult. The airway management apparatus 100 can mitigate such difficulty by producing a reasonable view of the tracheal inlet thereby allowing for placement of an endotracheal tube. Additionally, the curvature of the laryngoscopic blade 104 can change in real time while in the oral cavity via the controls to accommodate for normal variations in airway anatomy or pathologic airway conditions (e.g., tumors). By allowing for variation in the curvature of the blade 104 while within the oral cavity, changing the blade 104 to provide for variations in size and/or shape need not occur (e.g., reducing intubation time, . . . ). Further, trauma to the upper airway can be reduced by employing the airway management apparatus 100 and the physiologic stress on the patient associated with applying force on the tongue and oral cavity tissues can be lessened through a more efficient utilization of force and viewing angles. Moreover, the ability to visualize the vocal cords is often obstructed by the epiglottis covering the tracheal opening when employing conventional devices. In order to effectively overcome this obstacle, one can place the laryngoscope blade under the epiglottis to bring it out of the way or anteriorly displace the epiglottis by applying anteriorly directed force in the velecula, elevating the epiglottis with the adjoining soft tissue. Traditional laryngoscopes oftentimes fail to do this since to apply anterior force in the velecula requires the operator to "hinge" back on the blade, driving the proximal end of the blade into the patient's incisors. This can result in injury to the teeth, oral mucosa, or cause trauma to the lower part of the airway with adequately improving the view of the tracheal opening. In contrast, the portion of the blade 104 associated with fine control (e.g., tip of the blade 104) can pull the epiglottis out of the way to allow for viewing the vocal cords.

In addition to difficulty associated with visualization of the laryngeal aperture, once the anesthesia provider obtains a view, it is sometimes difficult to maneuver the endotracheal tube into the trachea to complete the process of securing an airway while employing conventional techniques. The airway management apparatus 100 can mitigate the maneuvering related difficulty by having a channel positioned along the side of the blade 104 that can include a ball bearing and spring-loaded pusher plate to dynamically adapt to variously size endotracheal tubes or airway intubation stylets. The channel can be positioned and/or adapt its position as the blade 104 articulates to deliver the tip of the endotracheal tube to the center of the camera viewing apparatus. This allows the operator to center the laryngeal aperture and watch under direct vision as the endotracheal tube passes into the trachea.

Moreover, in certain situations, patients may present with a physical exam that deems them as very challenging airways because of anatomic changes or pathologic tumors. In these situations, patients may need to have their airways secured without the addition of any anesthetic medications that may lead to sedation and a cessation of breathing or an obstruction of the patent airway that they initially presented with making things more urgent and often more difficult and stressful on the patient. Applying local anesthetics to these specific airways allows for the anesthesiologist to place a fiberoptic camera or gently place a laryngoscope to determine if it is safe to place the patient asleep prior to placing a breathing tube. The airway management apparatus 100 can have a channel that operates using Bernoulli principles to atomize liquid local anesthetic medications. This coupled with the camera system can allow one to completely topicallize the airway while the device is being placed resulting in a much more comfortable state of the patient as well as maintaining a spontaneously breathing state.

According to another example, a sleeve-type cover can be placed over the blade 104 and/or the handle 102 to enable reuse of the device without cleaning. According to an illustration, the sleeve-type cover can be disposable; however, it is to be appreciated that the cover can be sterilized to allow for reuse of the cover. Moreover, the cover can allow for the blade 104 to be articulated as well as data to be collected (e.g., via the cameras attached to the blade 104, . . . ) while mitigating obstruction thereof.

The blade 104 can include a main blade 106, a proximal blade 108, and a distal blade 110. The main blade 106 can be coupled to the handle 102. The main blade 106 and the proximal blade 108 can be coupled at a medium control articulation point 112, and the proximal blade 108 and the distal blade 110 can be coupled at a fine control articulation point 114. The proximal blade 108 can move with respect to the main blade 106 at the medium control articulation point 112. Further, the distal blade 110 can move with respect to the proximal blade 108 at the fine control articulation point 114.

The handle 102 can include the medium control component 116 and the fine control component 118. Movement of the proximal blade 108 with respect to the main blade 106 at the medium control articulation point 112 can be controlled by the medium control component 116. Further, movement of the distal blade 110 with respect to the proximal blade 108 at the fine control articulation point 114 can be controlled by the fine control component 118. For example, the medium control component 116 can be a knob, button, joystick, switch, dial, lever, touch screen, voice command, sensor, mouse, trigger, or the like. By way of another example, the fine control component 118 can be a knob, button, joystick, switch, dial, lever, touch screen, voice command, sensor, mouse, trigger, or the like.

By way of illustration, the size, shape, curvature, orientation, etc. of the blade 104 can be altered at the medium control articulation point 112 by the medium control component 116. Further, the size, shape, curvature, orientation, etc. of the blade 104 can be altered at the fine control articulation point 114 by the fine control component 118.

Figure 2:
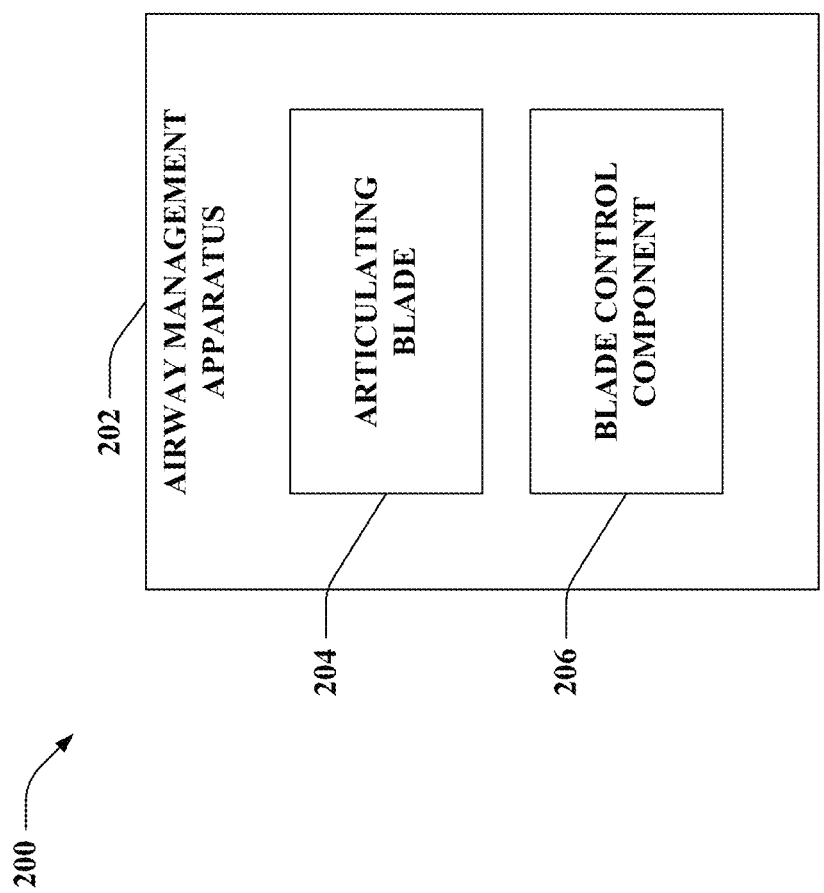
FIG. 2 illustrates a block diagram of an exemplary system that facilitates intubating a patient.

Turning to FIG. 2, illustrated is an example system 200 that facilitates intubating a patient. The system 200 includes an airway management apparatus 202 (e.g., the airway management apparatus 100 of FIG. 1) that enables performing direct laryngoscopy. The airway management apparatus 202 further includes an articulating blade 204 (e.g., the blade 104 of FIG. 1) and a blade control component 206 (e.g., included in the handle 102 of FIG. 1). For example, the blade control component 206 can include the medium control component 116 of FIG. 1 and/or the fine control component 118 of FIG. 1.

The articulating blade 204 can be manipulated in any manner. For instance, the size, length, shape, curvature, and the like of the articulating blade 204 or portion(s) thereof can be changed. By way of example, in contrast to some conventional devices with blades that have a fixed curvature, the curvature of the articulating blade 204 can be altered based upon anatomic characteristics of a patient. Further, such adjustments can be effectuated while positioning the airway management apparatus 202 proximate to the trachea within the oral cavity (e.g., as opposed to altering these features while the apparatus is removed from the patient's mouth and thereafter positioning the apparatus). The articulating blade 204 can accommodate variation in normal and abnormal anatomy of the upper airway. Moreover, the articulating blade 204 can reduce airway trauma and stimulation stress on the patient undergoing intubation. Additionally, the articulating blade 204 can be thinner than conventional blades employed in connection with typical laryngoscopic devices.

The articulating blade 204 can have any number of articulation points that can allow for varying degrees of control. For instance, a first articulation point (e.g., the medium control articulation point 112 of FIG. 1, . . . ) can allow for crudely obtaining a view of the vocal cords (e.g., by adjusting an angle of camera(s) to be directed at the vocal cords from the base of the tongue). Further, a second articulation point (e.g., the fine control articulation point 114 of FIG. 1, . . . ) can improve the crude view by manipulating the epiglottis of the patient.

The blade control component 206 can enable manipulating the articulating blade 204. The blade control component 206 can be included in a handle (e.g., the handle 102) of the airway management apparatus 202. The blade control component 206 can obtain substantially any type of input to yield a corresponding alteration of the articulating blade 204. For example, the blade control component 206 can receive an input from a user of the airway management apparatus 202 (e.g., via a knob, button, joystick, switch, dial, lever, touch screen, voice command, sensor, mouse, trigger, . . . ). According to another illustration, an input can be provided from a remotely located user via a signal; thus, telemedicine can be performed such that a user other than a user physically touching the airway management apparatus 202 can provide input utilized to manipulate the articulating blade 204. Moreover, the blade control component 206 can adjust the articulating blade 204 mechanically, via an electrical signal, and so forth. By way of illustration, the input can be utilized to control one or more motors to manipulate the articulating blade 204. For instance, servo motor(s) can leverage the input to smoothly control movement of the articulating blade 204 in substantially any number of planes. Additionally or alternatively, linear motor(s) can employ the input to manipulate the articulating blade 204. Thus, according to an example, the blade control component 206 can receive a user input, which can control servo motor(s) and/or linear motor(s) that can elongate, shorten, alter elevation, etc. associated with the articulating blade 204 or a portion thereof.

The articulating blade 204 can further include an adaptable channel (not shown). The adaptable channel can be adjusted in a size, shape, etc. (e.g., while the airway management apparatus 202 is being employed upon a patient). Also, the adaptable channel can allow for secure and directional placement of variously sized endotracheal tubes, intubating stylets, jet ventilation equipment, and the like. The adaptable channel can be employed to facilitate passing an endotracheal tube into the trachea under direct vision, for example.

The articulating blade 204 can also include a light transmission component (not shown) that can illuminate a patient's airway. For instance, controls (e.g., that alter on/off state, intensity, direction, wavelength, . . . ) for the light transmission component can be included in the handle of the airway management apparatus 202. Moreover, the light transmission component can be permanently affixed to, incorporated into, temporarily attached to (e.g., removable, replaceable, . . . ), etc. the articulating blade 204. Further, the articulating blade 204 can comprise an airway atomizing device, which can be used to deliver topical anesthesia during placement of an endotracheal tube.

Figure 3:
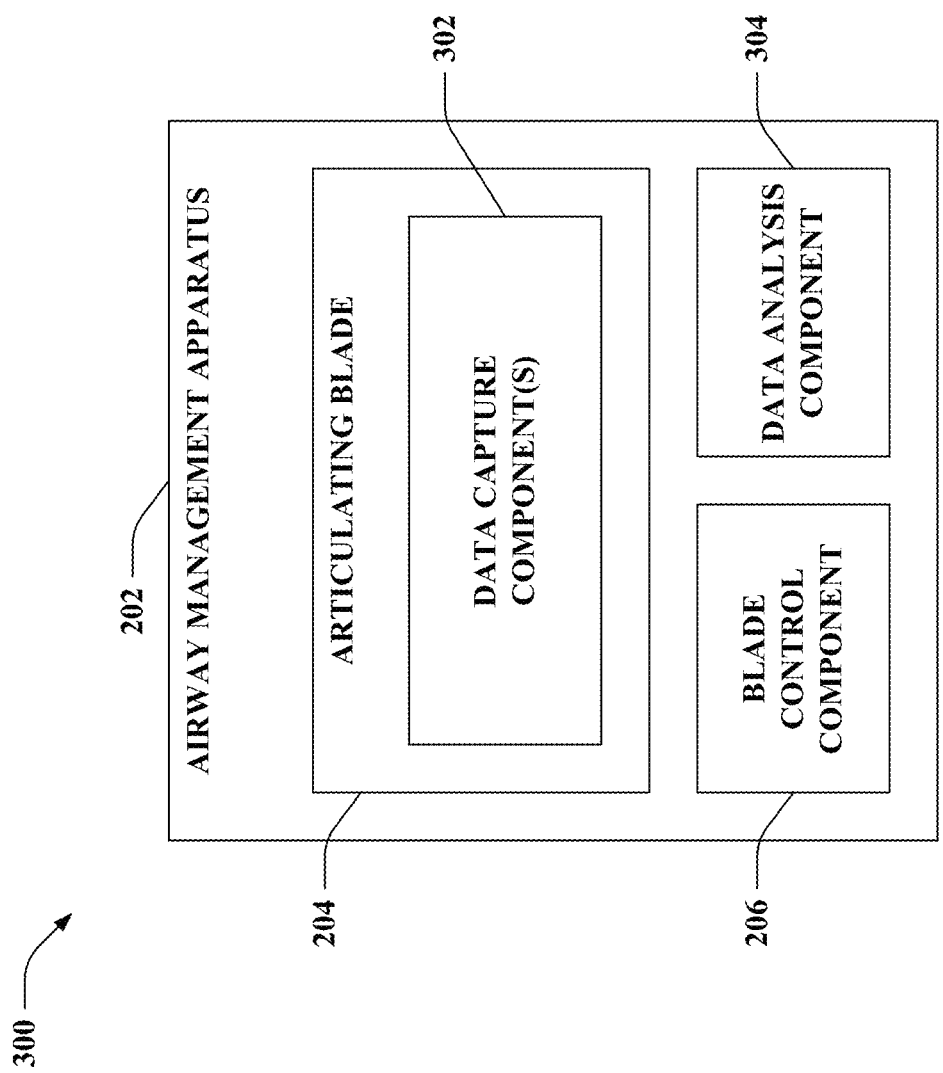
FIG. 3 illustrates a block diagram of an exemplary system that enables performing video laryngoscopy in accordance with various aspects.

Now turning to FIG. 3, illustrated is an example system 300 that enables performing video laryngoscopy in accordance with various aspects. The system 300 includes the airway management apparatus 202, which can further comprise the articulating blade 204 and the blade control component 206. The articulating blade 204 can also include data capture component(s) 302 that collect substantially any type of data (e.g., visual, audio, chemical, pressure, temperature, . . . ). It is contemplated that any number and/or type of data capture component(s) 302 can be utilized in connection with the airway management apparatus 202. A data analysis component 304 can further employ (e.g., aggregate, evaluate, . . . ) the data obtained by the data capture component(s) 302.

According to an example, the data capture component(s) 302 can be a plurality of cameras (e.g., two, more than two, . . . ) that can provide a stereoscopic view. The cameras can be located upon the articulating blade 204 at an articulation point that can be positioned at the base of the tongue looking up when the airway management apparatus 202 is utilized upon a patient. Thus, as opposed to conventional techniques where the vocal cords are viewed from outside of the mouth, the cameras can capture a view from the base of the tongue. The cameras can be any type of digital cameras including, for instance, charge coupled devices (CCDs) or CMOS sensors that can capture images. The data analysis component 304 can utilize the data obtained by these cameras to generate an image with depth perception that allows for focusing at various depths. The data analysis component 304 can enable stereoscopic visualization of the laryngeal aperture allowing for depth perception to improve endotracheal tube placement success. The data analysis component 304 can combine two or more images to create a composite image with depth (e.g., three dimensional), for example. Further, the data analysis component 304 can yield an output that can be transmitted, displayed, stored, matched to a pattern, etc.

It is contemplated that the data capture component(s) 302 can include any number of digital cameras. The digital camera(s) can be mounted on the articulating blade 204 and moved independently of the articulating blade 204 allowing for improved viewing of the laryngeal opening. These cameras can collect video data and/or still image data. Further, it is contemplated that the cameras can switch between collecting video and still images, simultaneously collect video and still images, or statically collect a particular type of data. Moreover, the cameras can be high definition cameras, for example. Further, the cameras can include a heating element (e.g., coil, light emitting diode, . . . ) to mitigate fogging while positioned within the oral cavity.

It is also contemplated that the data capture component(s) 302 can include a microphone that can record sounds, for example. By way of illustration, the sounds can include an operator's voice, which can be collected using the microphone to add notes, commentary, etc. corresponding to the videos and/or images collected by one or more digital cameras mounted on the articulating blade 204.

The data analysis component 304 can assemble data from the data capture component(s) 302. For example, a plurality of data capture component(s) 302 can provide input data to the data analysis component 304, which can thereafter aggregate such input data to yield a unified output. According to another illustration, the data analysis component 304 can perform pattern recognition upon the data from the data capture component(s) 302 to identify whether an endotracheal tube is properly positioned, misplaced, and so forth. Further to this illustration, an indication (e.g., alarm) of the recognized state can be yielded.

According to another example, the data capture component(s) 302 can be substantially any type of sensor and/or an interface that can connect with an externally located sensor. For instance, gaseous properties (e.g., carbon dioxide levels, . . . ) can be tracked by such sensors to provide feedback associated with placement of an endotracheal tube in the esophagus of a patient; thus, the monitored carbon dioxide level can be compared to a threshold (e.g., 2-3%, substantially any other percentage of carbon dioxide, . . . ) and, if the monitored level is below the threshold, the endotracheal tube can be determined to be positioned in the esophagus. Further, any other type of property (e.g., pH level, humidity, . . . ) can be monitored by these sensors to yield similar types of feedback. Moreover, the feedback can be evaluated by the data analysis component 304 to generate an associated output.

Figure 4:
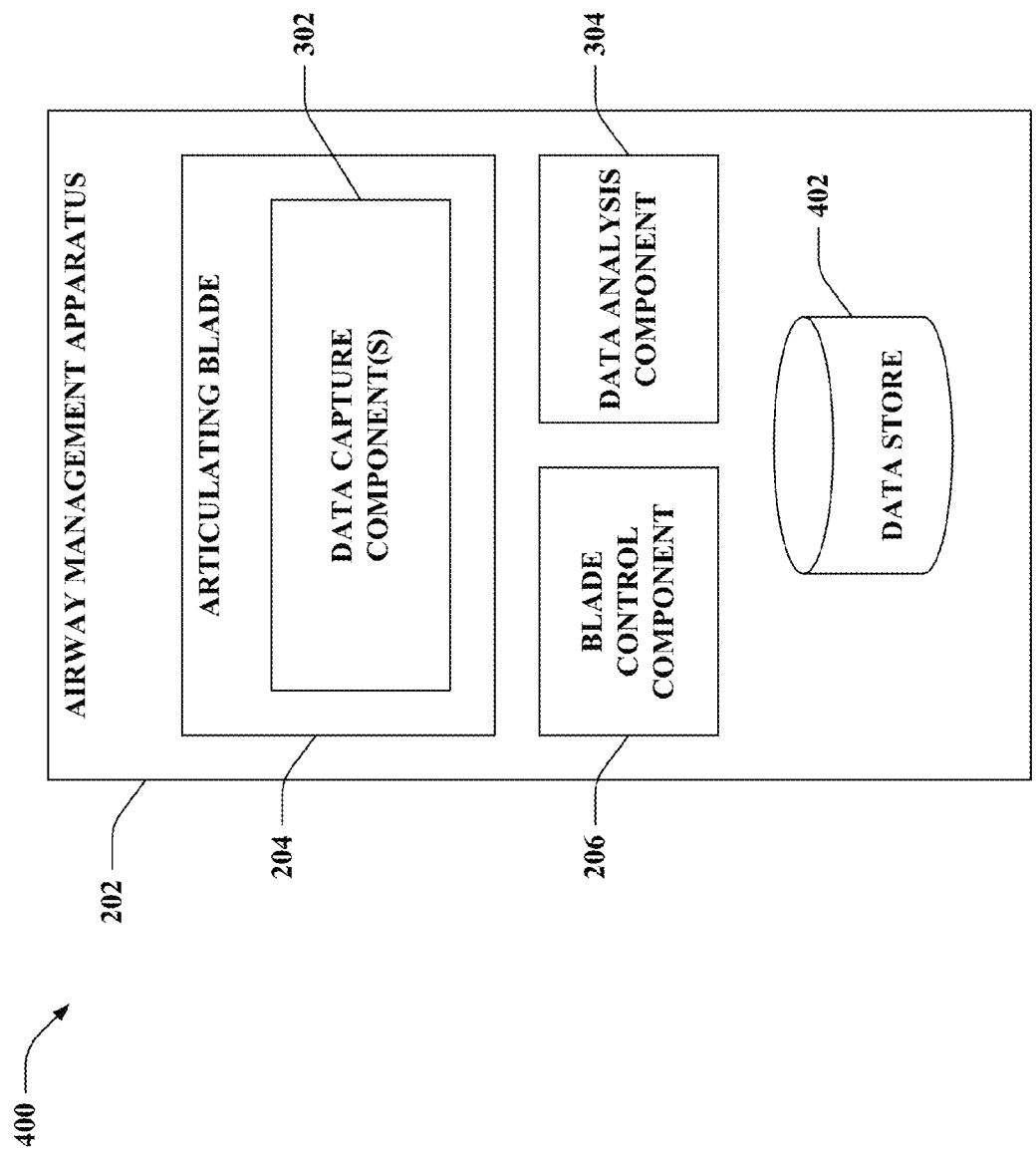
FIG. 4 illustrates a block diagram of an exemplary system that enables storing recorded data.

With reference to FIG. 4, illustrated is an example system 400 that enables storing recorded data. The system 400 includes the airway management apparatus 202, which can further comprise the articulating blade 204, the blade control component 206, and the data analysis component 304. Additionally, the articulating blade 204 can include the data capture component(s) 302. The airway management apparatus 202 can also include a data store 402 that can retain the data obtained by the data capture component(s) 302 and/or evaluated by the data analysis component 304.

The data store 402 can be, for example, either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable programmable ROM (EEPROM), or flash memory. Volatile memory can include random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), Rambus direct RAM (RDRAM), direct Rambus dynamic RAM (DRDRAM), and Rambus dynamic RAM (RDRAM). The data store 402 of the subject systems and methods is intended to comprise, without being limited to, these and any other suitable types of memory. In addition, it is to be appreciated that the data store 402 can be a server, a database, a hard drive, and the like.

By way of example, the data store 402 can be utilized to document difficult intubations. Thus, data such as images, video, alarms, and the like concerning such intubations can be retained in the data store 402. Accordingly, the data store 402 can be a flash memory chip that can be removed from the airway management apparatus 202 (e.g., from the handle) and placed in a patient's file. Additionally or alternatively, upon the airway management apparatus 202 being placed in a cradle, data retained in the data store 402 can be archived to hospital records (e.g., upon a server), printed in a report, etc. Further, the data can be archived via a wireless connection to such server. The data can be archived automatically, periodically, in response to a received request, and so forth. Further, it is contemplated that the data store 402 can similarly be included in any other type of medical device in addition to the airway management apparatus 202 to enable documenting procedures performed upon patients with these other types of medical devices.

Figure 5:
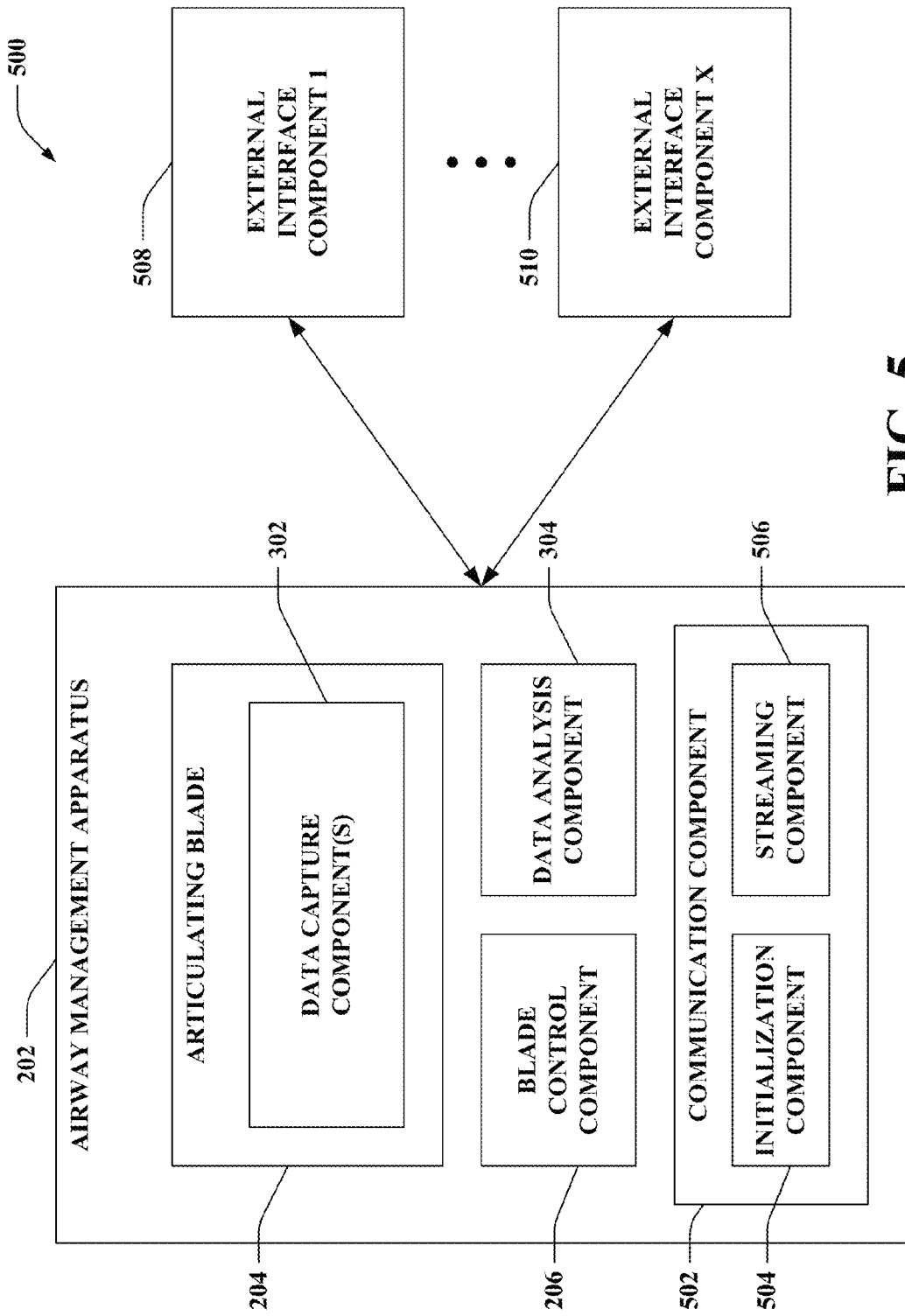
FIG. 5 illustrates a block diagram of an exemplary system that enables wirelessly transferring data captured from a laryngoscope.

Referring now to FIG. 5, illustrated is an example system 500 that enables wirelessly transferring data captured from a laryngoscope. The system 500 includes the airway management apparatus 202, which further comprises the articulating blade 204 (e.g., that further includes data capture component(s) 302), the blade control component 206, and data analysis component 304 as described above. The airway management apparatus 202 can also include a communication component 502 that can transmit and/or receive data within the system 500. The communication component 502 can further include an initialization component 504 and a streaming component 506. Moreover, the communication component 502 can enable the airway management apparatus 202 to communicate with one or more external interface components (e.g., an external interface component 1 508, . . . , an external interface component X 510, where X can be any integer).

The external interface components 508-510 can be, for example, cellular phones, smart phones, laptops, handheld communication devices, handheld computing devices, satellite radios, global positioning systems, personal digital assistants (PDAs), and/or any other suitable device. Additionally, the external interface components 508-510 can be any type of device with a monitor. The external interface components 508-510 can be located within proximity of the airway management apparatus 202. According to another example, one or more of the external interface components 508-510 can be positioned outside of a local vicinity of the airway management apparatus 202.

The initialization component 504 can determine whether any external interface components 508-510 are within range. Thus, a list of identities of these external interface components 508-510 can be populated by the initialization component 504. Thereafter, one or more of the listed external interface components 508-510 can be selected and data from the data analysis component 304 can be transmitted to the selected external interface component(s) 508-510 (e.g., which can thereafter output the data). For instance, the external interface component(s) 508-510 can visually display the output, yield audio output, and so forth.

Additionally, the initialization component 504 can allow for connecting to remotely located external interface components 508-510. For instance, the communication component 502 can enable communicating from the airway management apparatus 202 over an infrastructure based network (e.g., cellular network). Thus, a specially trained individual located anywhere in the world can be presented with feedback from the data capture component(s) 302. Further, this individual can control manipulation of the articulating blade 204 and/or the data capture component(s) 302 from the remote location.

By way of illustration, a monitor can be positioned in an operating room in which the airway management apparatus 202 is being employed. The initialization component 504 can identify that the monitor is within proximity and set up transfer of data to the monitor. For example, the monitor can automatically be initialized by the initialization component 504; thus, upon moving within range of the monitor, transmission can occur between the communication component 502 and the monitor to enable display upon the monitor of data collected by the airway management apparatus 202. Additionally or alternatively, the initialization component 504 can create a list of available devices (e.g., external interface components 508-510) including the monitor, and a selection may be made based upon a user input, a preference, a ranking, security levels, etc.

The streaming component 506 can enable real-time transfer of data from the data analysis component 304 to one or more of the external interface components 508-510. Thus, the streaming component 506 can allow for an image obtained with the data capture component(s) 302 from a patient's oral cavity to be displayed upon a PDA or any other external interface component 508-510 in real-time as the airway management apparatus 202 is manipulated within the oral cavity. Further, the streaming component 506 can allow for the data to be transmitted to a disparate device for storage (e.g., a remotely located data store).

The communication component 502 can utilize any type of wireless technology to transfer data (e.g., WiFi, 802.11b, g, n, Bluetooth, . . . ). Thus, the communication component 502 can enable wireless digital transmission of digital images to allow for remote viewing of airway manipulation, digital recording of procedures, porting images to video equipment in place such as anesthesiology monitoring or portable handle communication devices, and so forth. Moreover, the communication component 502 can receive feedback from one or more of the external interface components 508-510; such feedback can control manipulation of the articulating blade 204 by providing a signal to the blade control component 206, for example. Also, the feedback obtained by the communication component 502 can enable moving the data capture component(s) 302 (e.g., shifting the view being captured). Accordingly, this type of feedback can enable performing telemedicine.

The system 500 can further include an intelligent component (not shown) that can be employed by the airway management apparatus 202. For example, the intelligent component can infer which external interface component 508-510 within proximity to display data upon. Pursuant to another example, the intelligent component can infer potential errors in use associated with the airway management apparatus 202 (e.g., misplaced endotracheal tube, . . . ) and yield a corresponding alarm.

It is to be understood that the intelligent component can provide for reasoning about or infer states of the system, environment, and/or user from a set of observations as captured via events and/or data. Inference can be employed to identify a specific context or action, or can generate a probability distribution over states, for example. The inference can be probabilistic—that is, the computation of a probability distribution over states of interest based on a consideration of data and events. Inference can also refer to techniques employed for composing higher-level events from a set of events and/or data. Such inference results in the construction of new events or actions from a set of observed events and/or stored event data, whether or not the events are correlated in close temporal proximity, and whether the events and data come from one or several event and data sources. Various classification (explicitly and/or implicitly trained) schemes and/or systems (e.g., support vector machines, neural networks, expert systems, Bayesian belief networks, fuzzy logic, data fusion engines . . . ) can be employed in connection with performing automatic and/or inferred action in connection with the claimed subject matter.

A classifier is a function that maps an input attribute vector, x=(x1, x2, x3, x4, xn), to a confidence that the input belongs to a class, that is, f(x)=confidence(class). Such classification can employ a probabilistic and/or statistical-based analysis (e.g., factoring into the analysis utilities and costs) to prognose or infer an action that a user desires to be automatically performed. A support vector machine (SVM) is an example of a classifier that can be employed. The SVM operates by finding a hypersurface in the space of possible inputs, which hypersurface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and probabilistic classification models providing different patterns of independence can be employed. Classification as used herein also is inclusive of statistical regression that is utilized to develop models of priority.

Figure 6:
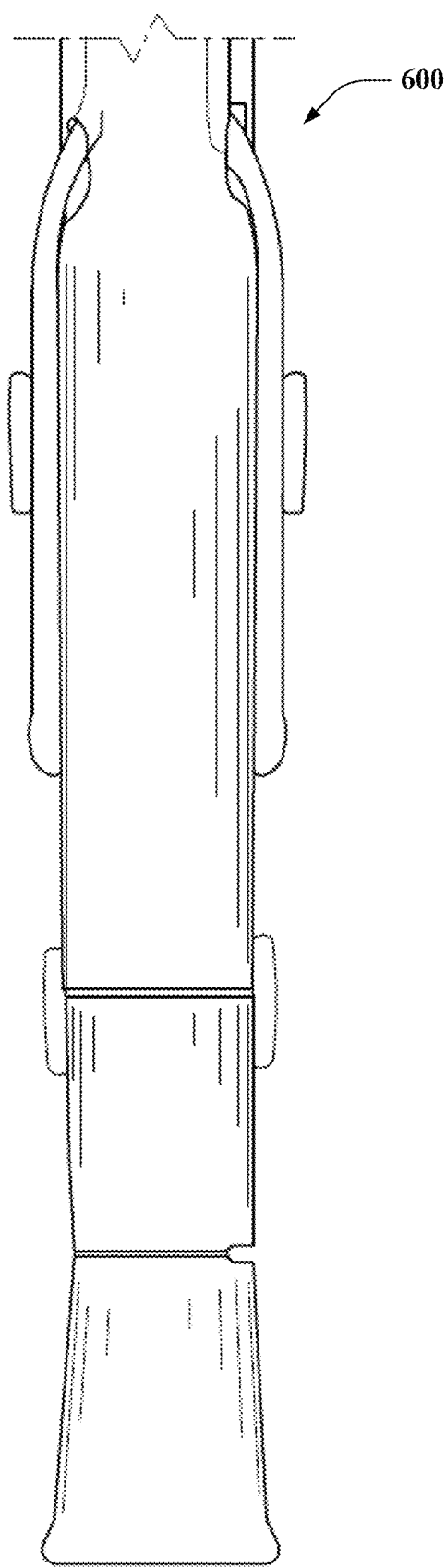
FIG. 6 illustrates another example schematic of an airway management apparatus in accordance with various aspects of the claimed subject matter.

Referring to FIG. 6, illustrated is another example schematic of an airway management apparatus 600. The schematic shown in FIG. 6 is a top view of the schematic depicted in FIG. 1.

Figure 7:
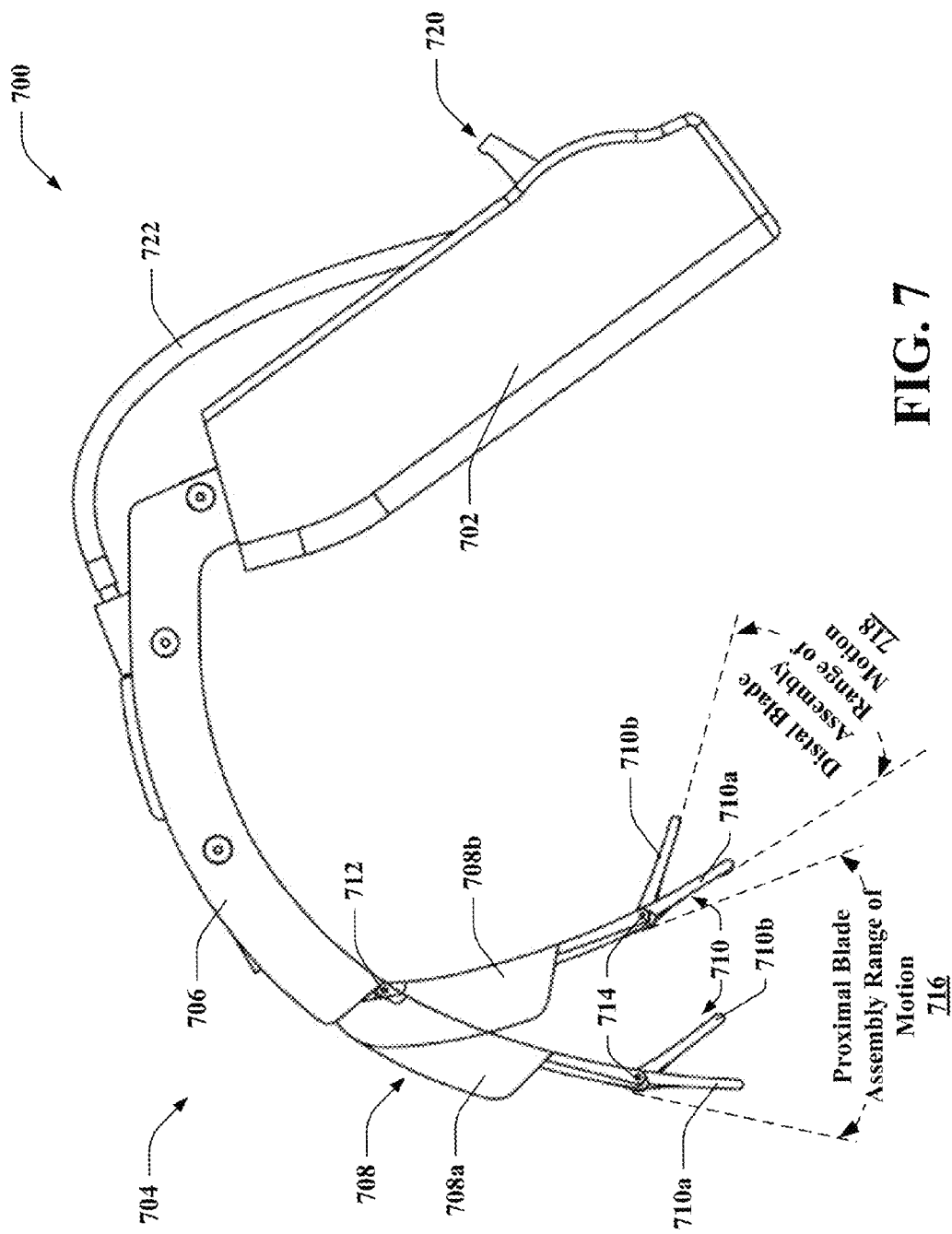
FIG. 7 illustrates a profile view of an example dynamic articulating laryngoscope.

Now turning to FIG. 7, illustrated is a profile view of a dynamic articulating laryngoscope 700 (e.g., the airway management apparatus 100 of FIG. 1, the airway management apparatus 202 of FIG. 2, . . . ). The dynamic articulating laryngoscope 700 can be controlled to configure to normal anatomic variants and pathologic abnormalities. The dynamic articulating laryngoscope 700 includes a handle assembly 702 (e.g., the handle 102 of FIG. 1, . . . ) coupled with a blade assembly 704 (e.g., the blade 104 of FIG. 1, the articulating blade 204 of FIG. 2, . . . ). It is contemplated that the handle assembly 702 and the blade assembly 704 can be removeably connected; yet, it is to be appreciated that the claimed subject matter is not so limited.

The blade assembly 704 can include a main blade assembly 706 (e.g., the main blade 106 of FIG. 1, . . . ), a proximal blade assembly 708 (e.g., the proximal blade 108 of FIG. 1, and a distal blade assembly 710 (e.g., the distal blade 110 of FIG. 1, . . . ). The main blade assembly 706 can be coupled to the handle assembly 702. Moreover, the main blade assembly 706 and the proximal blade assembly 708 can connect at a medium control articulation point 712 (e.g., the medium control articulation point 112 of FIG. 1, . . . ). Further, the proximal blade assembly 708 and the distal blade assembly 710 can connect at a fine control articulation point 714 (e.g., the fine control articulation point 114 of FIG. 1, . . . ).

The proximal blade assembly 708 can pivot with respect to the main blade assembly 706 at the medium control articulation point 712. FIG. 7 depicts the proximal blade assembly 708 in two positions: namely, an open position 708a of the proximal blade assembly 708 and a flex position 708b of the proximal blade assembly 708. It is to be appreciated that the description of the proximal blade assembly 708 is intended to cover the open position 708a and the flex position 708b as well as any position there between.

Moreover, the medium control articulation point 712 can allow the proximal blade assembly 708 to pivot relative to the main blade assembly 706 about the medium control articulation point 712 with a proximal blade assembly range of motion 716. The proximal blade assembly range of motion 716 is an angle of rotation (e.g., a maximum angle of rotation, . . . ) of the proximal blade assembly 708 between the open position 708a and the flex position 708b around the medium control articulation point 712. According to an example, the proximal blade assembly range of motion 716 can be less than 60 degrees. By way of another example, the proximal blade assembly range of motion 716 can be between 25 degrees and 45 degrees. Pursuant to a further example, the proximal blade assembly range of motion 716 can be between 30 degrees and 40 degrees. In accordance with yet another example, the proximal blade assembly range of motion 716 can be substantially equal to 35 degrees.

By way of illustration, the proximal blade assembly 708 can rotate about the medium control articulation point 712 relative to the main blade assembly 706 with the angle of rotation corresponding to the proximal blade assembly range of motion 716 (e.g., from the open position 708a to the flex position 708b, from the flex position 708b to the open position 708a, . . . ). Further, the proximal blade assembly 708 can pivot to and/or from any other position(s) between the open position 708a and the flex position 708b. Thus, according to another illustration, the proximal blade assembly 708 can rotate about the medium control articulation point 712 relative to the main blade assembly 706 with less than the angle of rotation corresponding to the proximal blade assembly range of motion 716.

The distal blade assembly 710 can pivot with respect to the proximal blade assembly 708 at the fine control articulation point 714. FIG. 7 depicts the distal blade assembly 710 in two positions when the proximal blade assembly 708 is in the open position 708a and the flex position 708b: more particularly, the distal blade assembly 710 is shown in an open position 710a and a flex position 710b. It is to be appreciated that the description of the distal blade assembly 710 is intended to cover the open position 710a and the flex position 710b as well as any position there between.

The fine control articulation point 714 can allow the distal blade assembly 710 to pivot relative to the proximal blade assembly 708 about the fine control articulation point 714 with a distal blade assembly range of motion 718. The distal blade assembly range of motion 718 is an angle of rotation (e.g., a maximum angle of rotation, . . . ) of the distal blade assembly 710 between the open position 710*a* and the flex position 710*b* around the fine control articulation point 714. According to an example, the distal blade assembly range of motion 718 can be less than 60 degrees. By way of another example, the distal blade assembly range of motion 718 can be between 30 degrees and 50 degrees. Pursuant to a further example, the distal blade assembly range of motion 718 can be between 35 degrees and 45 degrees. In accordance with yet another example, the distal blade assembly range of motion 718 can be substantially equal to 40 degrees.

By way of illustration, the distal blade assembly 710 can rotate about the fine control articulation point 714 relative to the proximal blade assembly 708 with the angle of rotation corresponding to the distal blade assembly range of motion 718 (e.g., from the open position 710*a* to the flex position 710*b*, from the flex position 710*b* to the open position 710*a*, . . . ). Further, the distal blade assembly 710 can pivot to and/or from any other position(s) between the open position 710*a* and the flex position 710*b*. Thus, according to another illustration, the distal blade assembly 710 can rotate about the fine control articulation point 714 relative to the proximal blade assembly 708 with less than the angle of rotation corresponding to the distal blade assembly range of motion 718.

Moreover, the handle assembly 702 can include one or more blade control components 720 (the medium control component 116 of FIG. 1, the fine control component 118 of FIG. 1, the blade control component 206 of FIG. 2, . . . ) that manipulate the size, length, shape, curvature, and the like of the blade assembly 704 (or portions thereof). The one or more blade control components 720 can control pivoting of the blade assembly 704 at the medium control articulation point 712 and/or the fine control articulation point 714 as described above.

According to another example, although not shown, it is contemplated that one or more cameras can be integrated into the blade assembly 704, mounted upon the blade assembly 704, removeably connected to the blade assembly 704, or the like. The one or more cameras can be positioned nearby the medium control articulation point 712. It is contemplated that the one or more cameras can be maneuvered independently from the blade assembly 704, for example. Thus, at least one of the one or more blade control components 720 can control operation of the one or more cameras (e.g., changing orientation of the one or more cameras with respect to the blade assembly 704, . . . ) to enable viewing of the laryngeal opening. Yet, according to another example, it is to be appreciated that the one or more cameras can be in a fixed orientation with respect to the blade assembly 704; following this example, manipulation of the blade assembly 704 can allow for changing the view captured by the one or more cameras to enable viewing of the laryngeal opening.

According to various examples described herein, the dynamic articulating laryngoscope 700 can include a flexible shaft 722. As set forth in greater detail below, the flexible shaft 722 can be driven by an electric motor (e.g., included in the handle assembly 702, . . . ) to effectuate pivoting of the proximal blade assembly 708 relative to the main blade assembly 706 about the medium control articulation point 712. Yet, pursuant to other examples described herein, the dynamic articulating laryngoscope 700 need not include the flexible shaft 722; rather, pivoting of the proximal blade assembly 708 with respect to the main blade assembly 706 around the medium control articulation point 712 can be effectuated similarly to pivoting of the distal blade assembly 710 relative to the proximal blade assembly 708 about the fine control articulation point 714 (e.g., using a pusher pinned to the distal blade assembly 710, . . . ) described in more detail below.

The dynamic articulating laryngoscope 700 can include two articulating points (e.g., the medium control articulation point 712 and the fine control articulation point 714, . . . ) in the blade assembly 704; yet, although not shown, it is also contemplated that the dynamic articulating laryngoscope 700 can include more than two articulating points. The medium control articulation point 712 and the fine control articulation point 714 can be positioned to enable movement of soft tissue that can obstruct a view seen through the incorporated camera(s). Moreover, the blade assembly 704 of the dynamic articulating laryngoscope 700 can allow for fine control of tissue retraction within the upper airway, thus providing for an improved view of the vocal cords without the need to lever the handle assembly 702, and potentially compromise space available to pass an endotracheal tube.

In contrast, convention laryngoscopes oftentimes have a fixed-angle blade, mostly resembling the shape of a standard Macintosh blade. With typical laryngoscopes, optimal glottic visualization can depend upon advancement and/or manipulation of the laryngoscope, while the blade remains at a fixed angle. Such advancement and/or manipulation of the laryngoscope, however, can make intubation more difficult by reducing space available to pass an endotracheal tube. In addition, upper airway anatomic variations (e.g., anterior position of the larynx, large tongue, short sternothyroid distance, . . . ) often make visualization of the glottic opening difficult at best.

Figure 8:
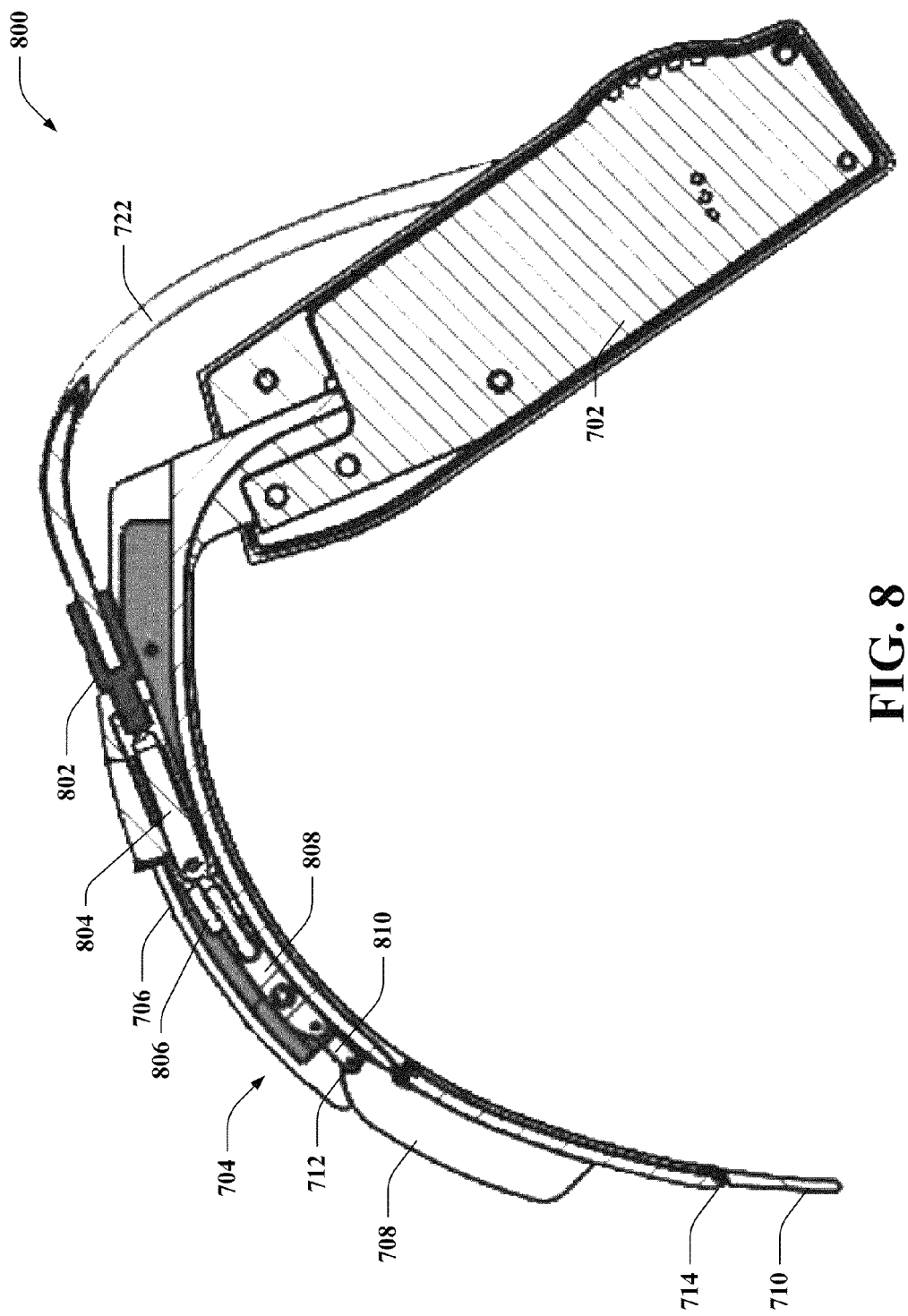
FIG. 8 illustrates a profile view of an example dynamic articulating laryngoscope that includes a flexible shaft.

With reference to FIG. 8, illustrated is a profile view of a dynamic articulating laryngoscope 800 (e.g., the airway management apparatus 100 of FIG. 1, the airway management apparatus 202 of FIG. 2, the dynamic articulating laryngoscope 700 of FIG. 7, . . . ) that includes the flexible shaft 722. The dynamic articulating laryngoscope 800 includes the handle assembly 702 and the blade assembly 704. Further, the blade assembly 704 can include the main blade assembly 706, the proximal blade assembly 708, and the distal blade assembly 710. The medium control articulation point 712 can join the main blade assembly 706 and the proximal blade assembly 708, and the fine control articulation point 714 can join the proximal blade assembly 708 and the distal blade assembly 710. Further, FIG. 8 depicts a cut-away view that reveals features that can control movement of the proximal blade assembly 708 with respect to the main blade assembly 706 about the medium control articulation point 712.

According to an illustration, the handle assembly 702 can include a motor (e.g., servo motor, electric motor, . . . ) that can drive the flexible shaft 722 (e.g., based upon an input, . . . ). Driving of the flexible shaft 722 by the motor can be controlled by a medium control component (e.g., the medium control component 116 of FIG. 1, the blade control component 206 of FIG. 2, . . . ). The flexible shaft 722 can be coupled to a shaft adapter 802. The shaft adapter 802 can further be coupled to a lead screw 804. The lead screw 804 can further be coupled to a lead screw adapter 806. Moreover, the lead screw adapter 806 can be coupled to a sliding link 808. The sliding link 808 can further be coupled to a rotating link 810. Moreover, the rotating link 810 can be coupled to the proximal blade assembly 708 at the medium control articulation point 712. For example, the rotating link 810 can be pinned to the proximal blade assembly 708 at the medium control articulation point 712.

Pursuant to an example, two lead screws can be included in the dynamic articulating laryngoscope 800. Following this example, a rotating lead screw can be coupled to the shaft adapter 802 and a fixed lead screw can be coupled to the lead screw adapter 806. Yet, the claimed subject matter is not so limited.

The dynamic articulating laryngoscope 800 can convert rotary motion supplied by the flexible shaft 722 to pivot the proximal blade assembly 708 with respect to the main blade assembly 706 about the medium control articulation point 712. Pursuant to an illustration, the medium control component can receive an input, which can cause the motor to drive the flexible shaft 722. The flexible shaft 722 can cause the lead screw 804 to rotate. The lead screw 804 can translate the radial motion of the rotation into linear motion. Thus, the lead screw 804 can move the sliding link 808 (e.g., by moving the lead screw adapter 806, . . . ) along the length of the main blade assembly 706 (e.g., towards the medium control articulation point 712, away from the medium control articulation point 712, . . . ). Such movement of the sliding link 808 along the length of the main blade assembly 706 can cause the rotating link 810 to pivot the proximal blade assembly 708 about the medium control articulation point 712 (e.g., rotate in a direction towards the open position 708a of FIG. 7, rotate in a direction towards the flex position 708b of FIG. 7, . . . ).

Figure 9:
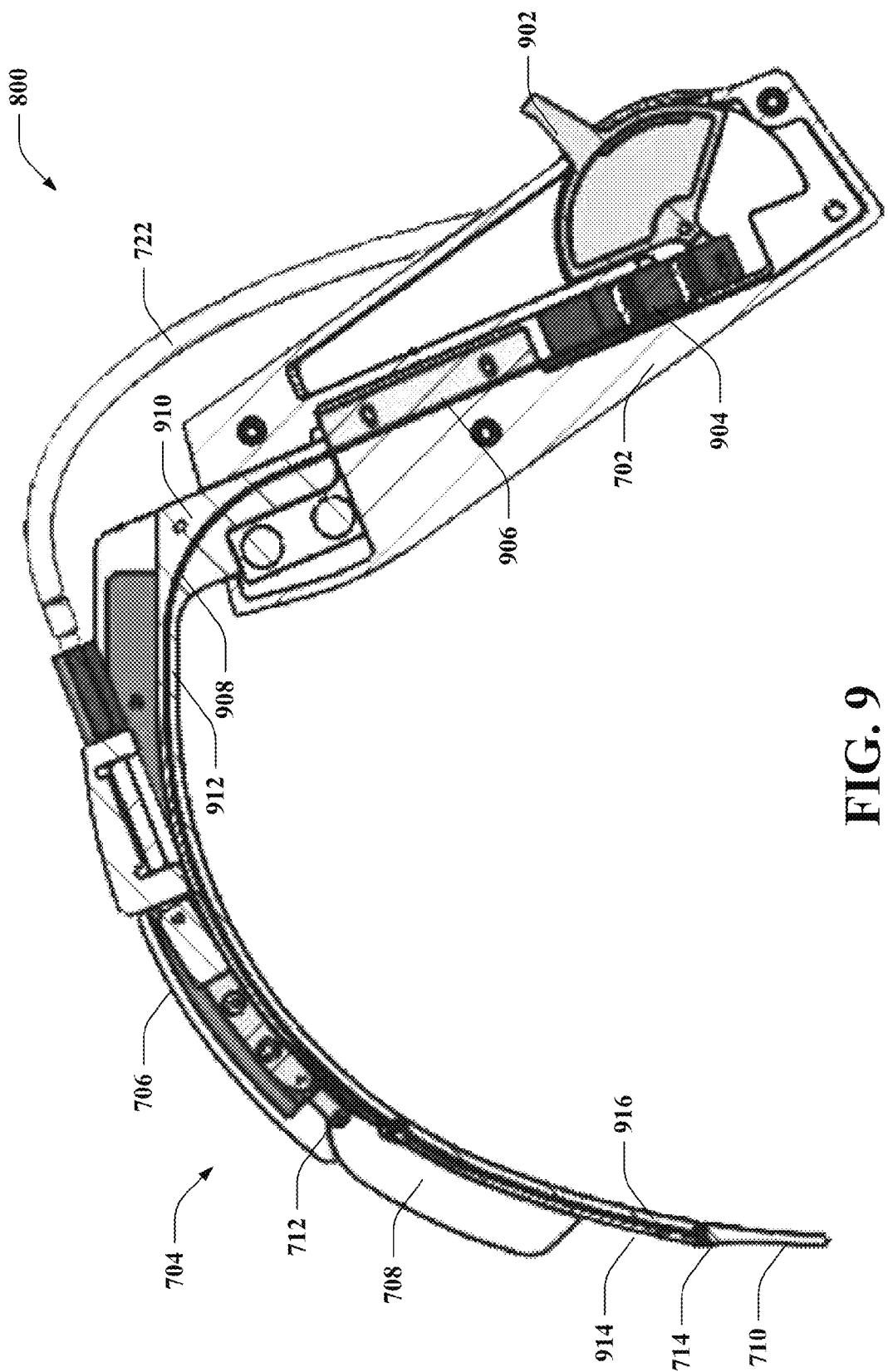
FIG. 9 illustrates another profile view of the dynamic articulating laryngoscope that includes the flexible shaft.

Now referring to FIG. 9, illustrated is another profile view of the dynamic articulating laryngoscope 800 that includes the flexible shaft 722. FIG. 9 depicts a cut-away view that reveals features that can control movement of the distal blade assembly 710 with respect to the proximal blade assembly 708 about the fine control articulation point 714.

The handle assembly 702 can include a knob 902 (e.g., the fine control component 118 of FIG. 1, the blade control component 206 of FIG. 2, . . . ) coupled to a lever block 904. The lever block 904 can move within a channel formed as part of a handle chassis (included in the handle assembly 702). Moreover, a channel block 906 can be secured within the channel formed as part of the handle chassis; the channel block 906 can stop the movement of the lever block 904 within the channel in a direction towards the blade assembly 704 to limit a range of motion of the lever block 904 within the channel. Moreover, the lever block 904 can be coupled to one end of a pusher 908. Another end of the pusher 908 can be coupled to the distal blade assembly 710 at the fine control articulation point 714. By way of example, the pusher 908 can be pinned to the distal blade assembly 710 at the fine control articulation point 714.

The pusher 908 can be constructed of substantially any adaptable, flexible material. The flexibility can enable the pusher 908 to be slid within a channel that curves within the handle assembly 702 and the blade assembly 704. Moreover, as the pusher 908 is slid as initiated by manipulation of the knob 902, the pusher 908 can yield a force (e.g., pushing or pulling, . . . ) upon a pin included in the fine control articulation point 714, which can result in the distal blade assembly 710 rotating around the fine control articulation point 714. Thus, the pusher 908 can be constructed of a material that provides strength to yield such force.

Further, the pusher 908 can be packaged between blade covers and blades. For instance, the main blade assembly 706 can include a main blade cover 910 and a main blade 912. The pusher 908 can be positioned between the main blade cover 910 and the main blade 912. Moreover, the proximal blade assembly 708 can include a proximal blade cover 914 and a proximal blade 916. The pusher 908 can be positioned between the proximal blade cover 914 and the proximal blade 916. Further, a channel can be formed between the blade covers and the blades (e.g., the main blade cover 910 and the main blade 912 can form a portion of the channel, the proximal blade cover 914 and the proximal blade 916 can form another portion of the channel, . . . ); thus, the pusher 908 can be manipulated (e.g., slide, . . . ) through such channel (e.g., the pusher 908 can be slidable within such channel, . . . ).

According to an example, the knob 902 can be rotated (e.g., by a user, . . . ), which can cause the lever block 904 to slide within the channel formed as part of the handle chassis. As the lever block 904 moves within the channel, the pusher 908 also moves. By way of illustration, if the knob 902 is rotated such that the lever block 904 moves towards the blade assembly 704 within the channel, then the pusher 908 is similarly advanced in the direction towards the blade assembly 704. Accordingly, the pusher 908 slides between the main blade cover 910 and the main blade 912 as well as between the proximal blade cover 914 and the proximal blade 916 towards the distal blade assembly 710. Such sliding of the pusher 908 can cause the distal blade assembly 710 to rotate around the fine control articulation point 714 (e.g., in a direction towards the flex position 710b of FIG. 7, . . . ). According to another illustration, if the knob 902 is rotated such that the lever block 904 moves away from the blade assembly 704 within the channel, then the pusher 908 similarly moves in the direction away from the blade assembly 704. Hence, the pusher 908 slides between the main blade cover 910 and the main blade 912 as well as between the proximal blade cover 914 and the proximal blade 916 away from the distal blade assembly 710. Such sliding of the pusher 908 can cause the distal blade assembly 710 to rotate around the fine control articulation point 714 (e.g., in a direction towards the open position 710a of FIG. 7, . . . ).

Figure 10:
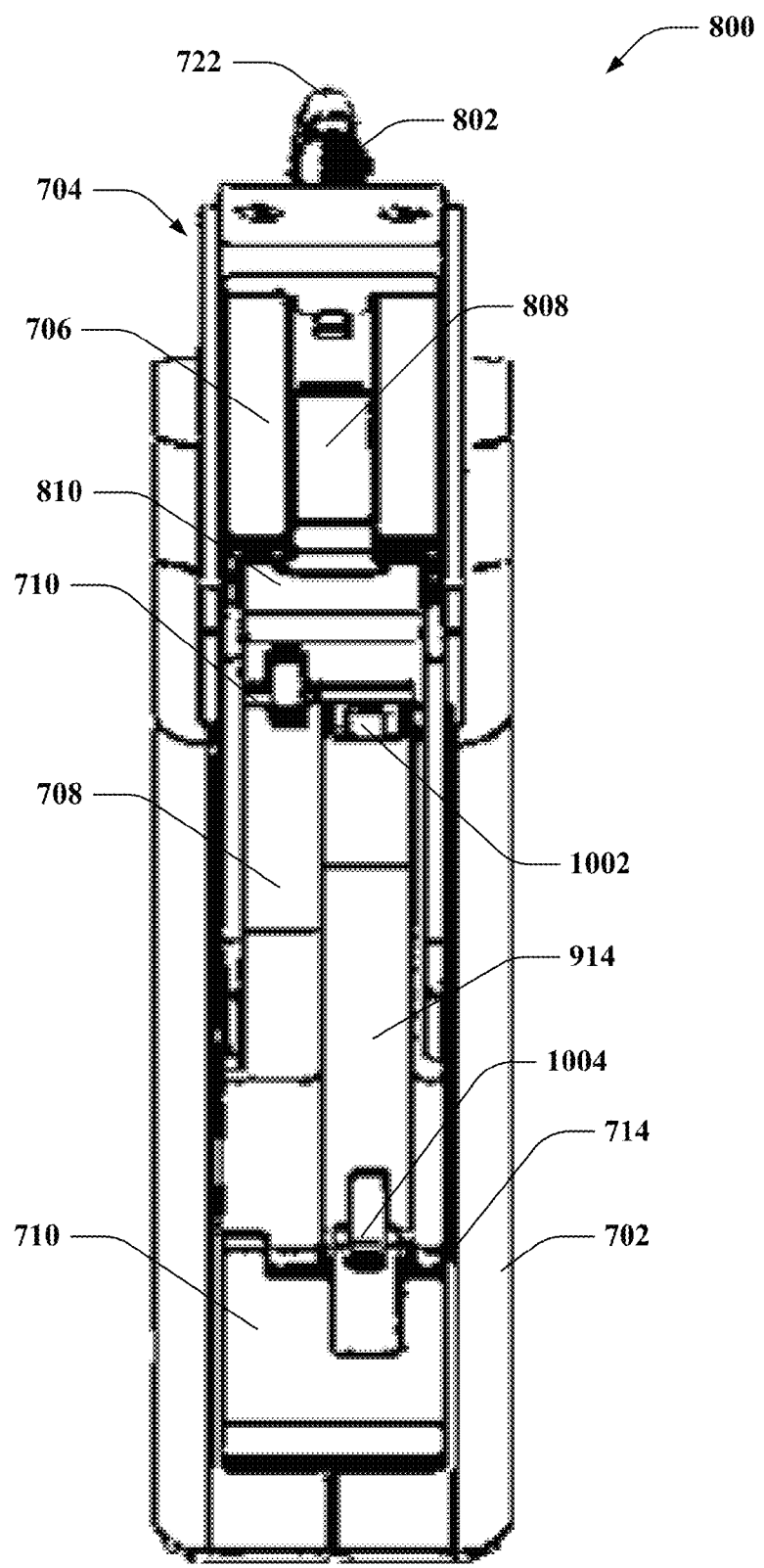
FIG. 10 illustrates a front view of the dynamic articulating laryngoscope that includes the flexible shaft.

Turning to FIG. 10, illustrated is a front view of the dynamic articulating laryngoscope 800 that includes the flexible shaft 722 looking at the blade assembly 704 with the handle assembly 702 positioned behind. The pusher 908 (not shown) can pass through a junction 1002 included in the medium control articulation point 712. Further, the pusher 908 can connect to the distal blade assembly 710 with a pin 1004 included in the fine control articulation point 714. Moreover, along the length of the proximal blade assembly 708, the pusher 908 can be located below the proximal blade cover 914.

Figure 11:
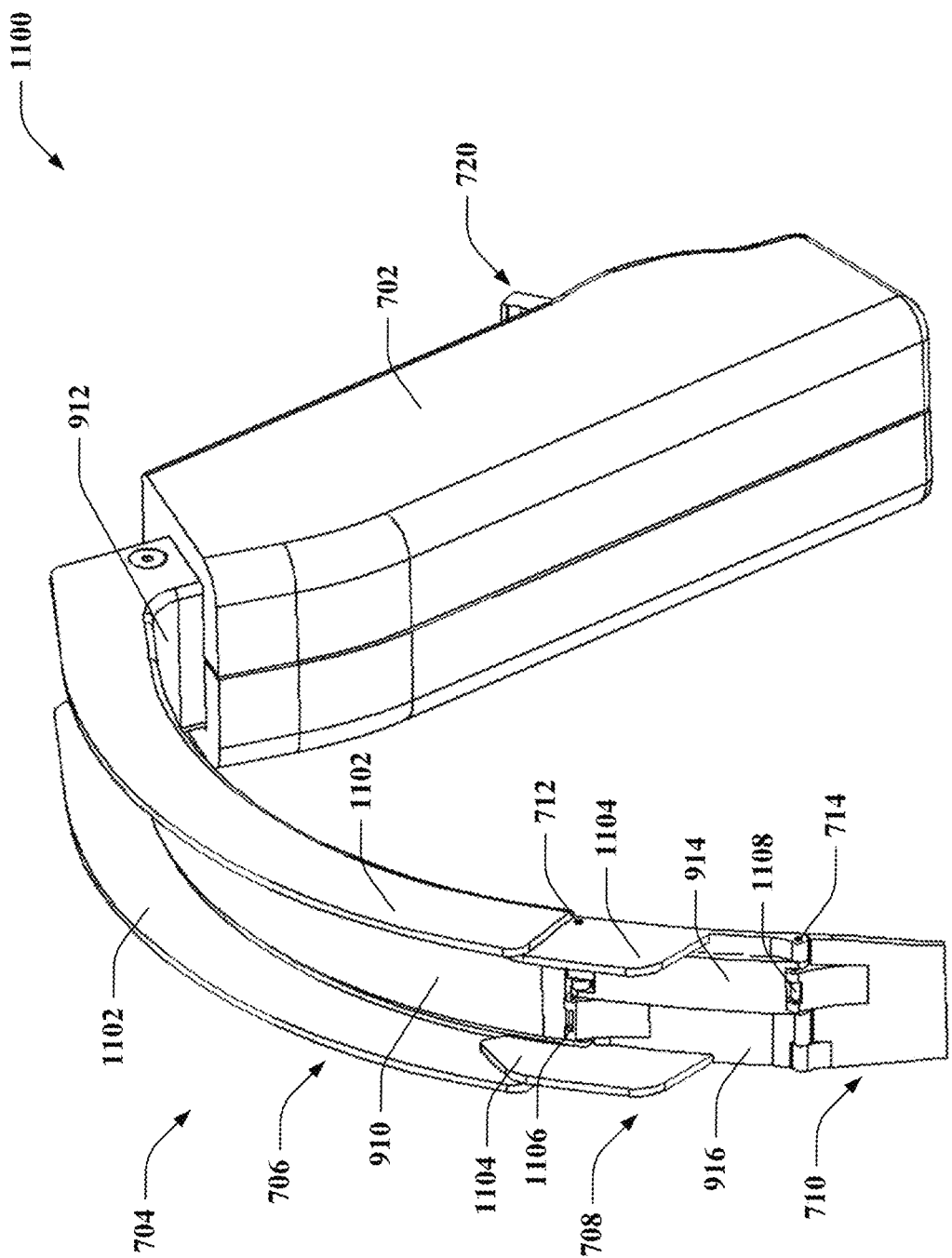
FIGS. 11-14 illustrate isometric views of another example dynamic articulating laryngoscope.

Referring to FIG. 11, illustrated is an isometric view of a dynamic articulating laryngoscope 1100 (e.g., the airway management apparatus 100 of FIG. 1, the airway management apparatus 202 of FIG. 2, the dynamic articulating laryngoscope 700 of FIG. 7, . . . ). The dynamic articulating laryngoscope 1100 need not include the flexible shaft 722 described herein. Thus, operation of the medium control articulation point 712 can be substantially similar to operation of the fine control articulation point 714. Yet, it is to be appreciated that various aspects described in conjunction with the dynamic articulating laryngoscope 800 that includes the flexible shaft 722 can be extended to the dynamic articulating laryngoscope 1100. Similarly, it is contemplated that various aspects described in conjunction with the dynamic articulating laryngoscope 1100 can be extended to the dynamic articulating laryngoscope 800.

The dynamic articulating laryngoscope 1100 includes the handle assembly 702 (e.g., including the one or more blade control components 720, . . . ) and the blade assembly 704. Further, the blade assembly 704 includes the main blade assembly 706, the proximal blade assembly 708, and the distal blade assembly 710. The medium control articulation point 712 can connect the main blade assembly 706 and the proximal blade assembly 708. Further, the fine control articulation point 714 can connect the proximal blade assembly 708 and the distal blade assembly 710.

The main blade assembly 706 can include the main blade cover 910 and the main blade 912. Moreover, the main blade assembly 706 can include main blade flanges 1102. Further, the proximal blade assembly 708 can include the proximal blade cover 914, the proximal blade 916, and proximal blade flanges 1104. The main blade flanges 1102 and the proximal blade flanges 1104 can provide sidewalls for the dynamic articulating laryngoscope 1100, thereby yielding an adaptable channel through which a stylet, intubation tube, or the like can be passed. Moreover, although not described, it is to be appreciated that the dynamic articulating laryngoscope 800 can similarly include the main blade flanges 1102 and the proximal blade flanges 1104, which can form the adaptable channel.

Further, the dynamic articulating laryngoscope 1100 can include two pushers (not shown). The two pushers can be substantially similar to the pusher 908 of FIG. 9. For instance, a proximal pusher can be utilized to pivot the proximal blade assembly 708 in relation to the main blade assembly 706 about the medium control articulation point 712, while a distal pusher (e.g., the pusher 908 of FIG. 9, . . . ) can be utilized to pivot the distal blade assembly 710 in relation to the proximal blade assembly 708 about the fine control articulation point 714. The two pushers can be manipulated by respective blade control components 720 (e.g., respective knobs, . . . ) included in the handle assembly 702. The two pushers can be positioned under the main blade cover 910 of the main blade assembly 706. The proximal pusher can connect with the proximal blade assembly 708 at the medium control articulation point 712 with a pin 1106. Moreover, the distal pusher can pass through the medium control articulation point 712 and further be positioned under the proximal blade cover 914. The distal pusher can connect with the distal blade assembly 710 at the fine control articulation point 714 with a pin 1108.

Figure 12:
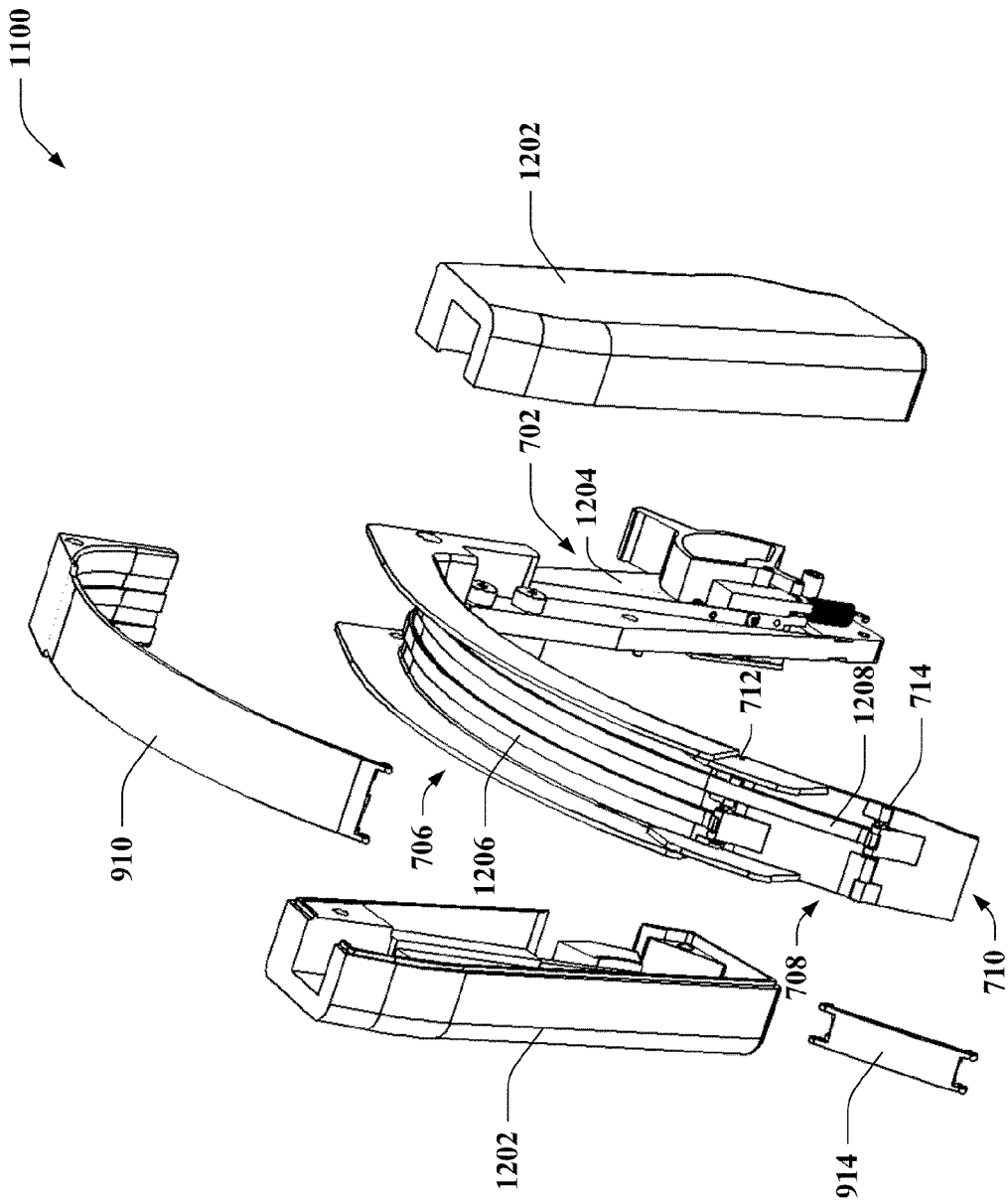

With reference to FIG. 12, illustrated is another isometric view of the dynamic articulating laryngoscope 1100. FIG. 12 shows handle covers 1202 being removed from the handle assembly 702 to reveal a handle chassis 1204 in addition to other features. Further, a channel block is not depicted in FIG. 12 (as well as FIGS. 13 and 14); yet, it is to be appreciated that a channel block (e.g., the channel block 906 of FIG. 9, . . . ) can be positioned at a top of a channel formed as part of the handle chassis 1204. FIG. 12 also depicts the main blade cover 910 being removed from the main blade assembly 706 and the proximal blade cover 914 being removed from the proximal blade assembly 708. Thus, a proximal pusher 1206 and a distal pusher 1208 typically positioned below the main blade cover 910 and/or the proximal blade cover 914 are viewable.

Figure 13:
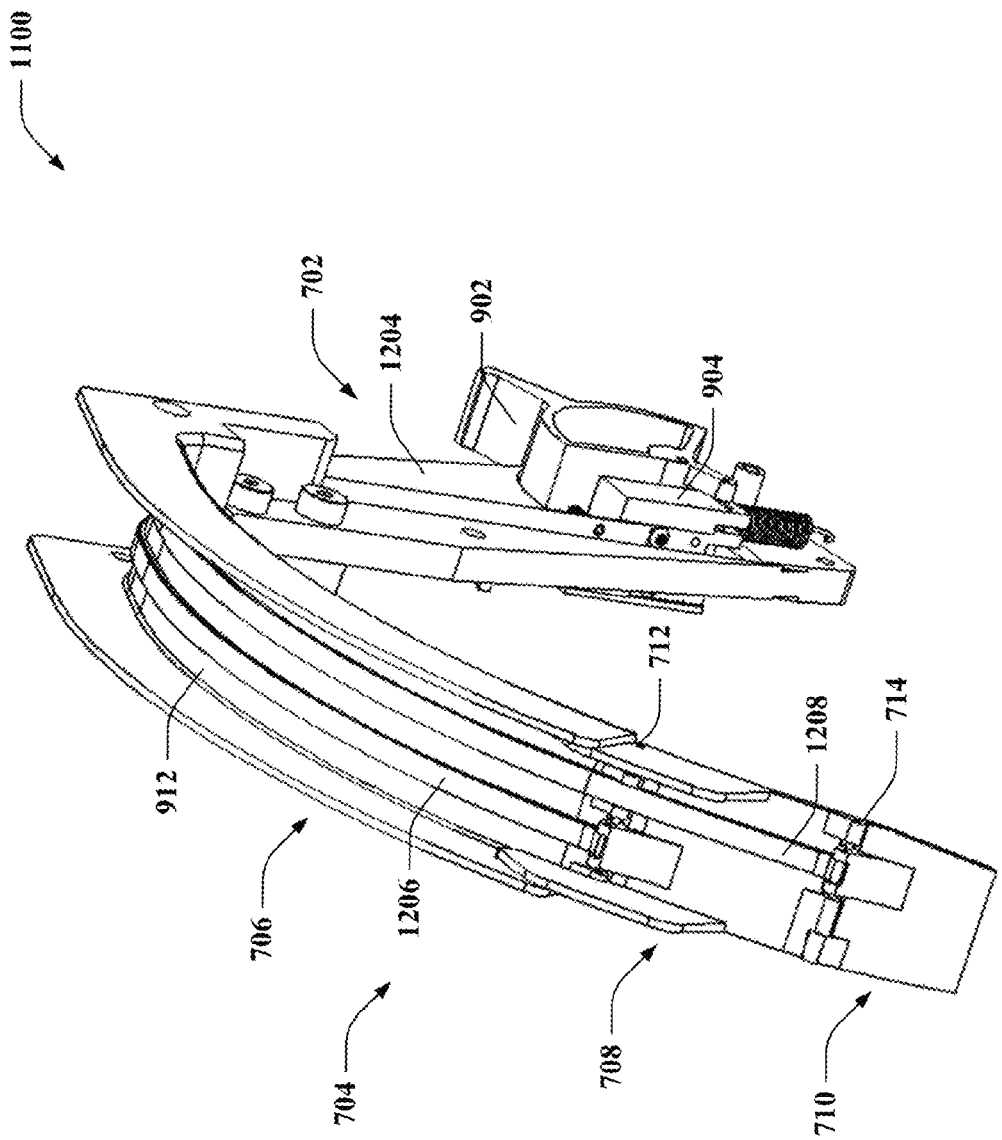

Turning to FIG. 13, illustrated is yet another isometric view of the dynamic articulating laryngoscope 1100. The handle assembly 702 includes the knob 902 and the lever block 904. The lever block 904 can be coupled to the distal pusher 1208. Moreover, the handle assembly 702 includes the handle chassis 1204. The handle assembly 702 can also include a disparate knob and a disparate lever block (on the other side of the handle chassis 1204), where the disparate lever block can similarly be coupled to the proximal pusher 1206. It is to be appreciated that the discussion herein related the knob 902 and the lever block 904 can be extended to the disparate knob and the disparate lever block coupled to the proximal pusher 1206.

The distal pusher 1208 can be slid along the length of the blade assembly 704 to rotate the distal blade assembly 710 with respect to the proximal blade assembly 708 around the fine control articulation point 714. For example, the knob 902 can be manipulated in a first direction (e.g., rotated downwards, . . . ), which can move the lever block 904 towards the blade assembly 704. Since the distal pusher 1208 can be attached to the lever block 904, the distal pusher 1208 can be slid along the length of the blade assembly 704 towards the fine control articulation point 714, which can cause the distal blade assembly 710 to pivot around the fine control articulation point 714 towards the flex position 710b of FIG. 7. According to another example, the knob 902 can be manipulated in a second direction (e.g., rotated upwards, . . . ), which can move the lever block 904 away from the blade assembly 704. Thus, the distal pusher 1208 can be slid along the length of the blade assembly 704 away from the fine control articulation point 714, which can cause the distal blade assembly 710 to pivot around the fine control articulation point 714 towards the open position 710a of FIG. 7.

Figure 14:
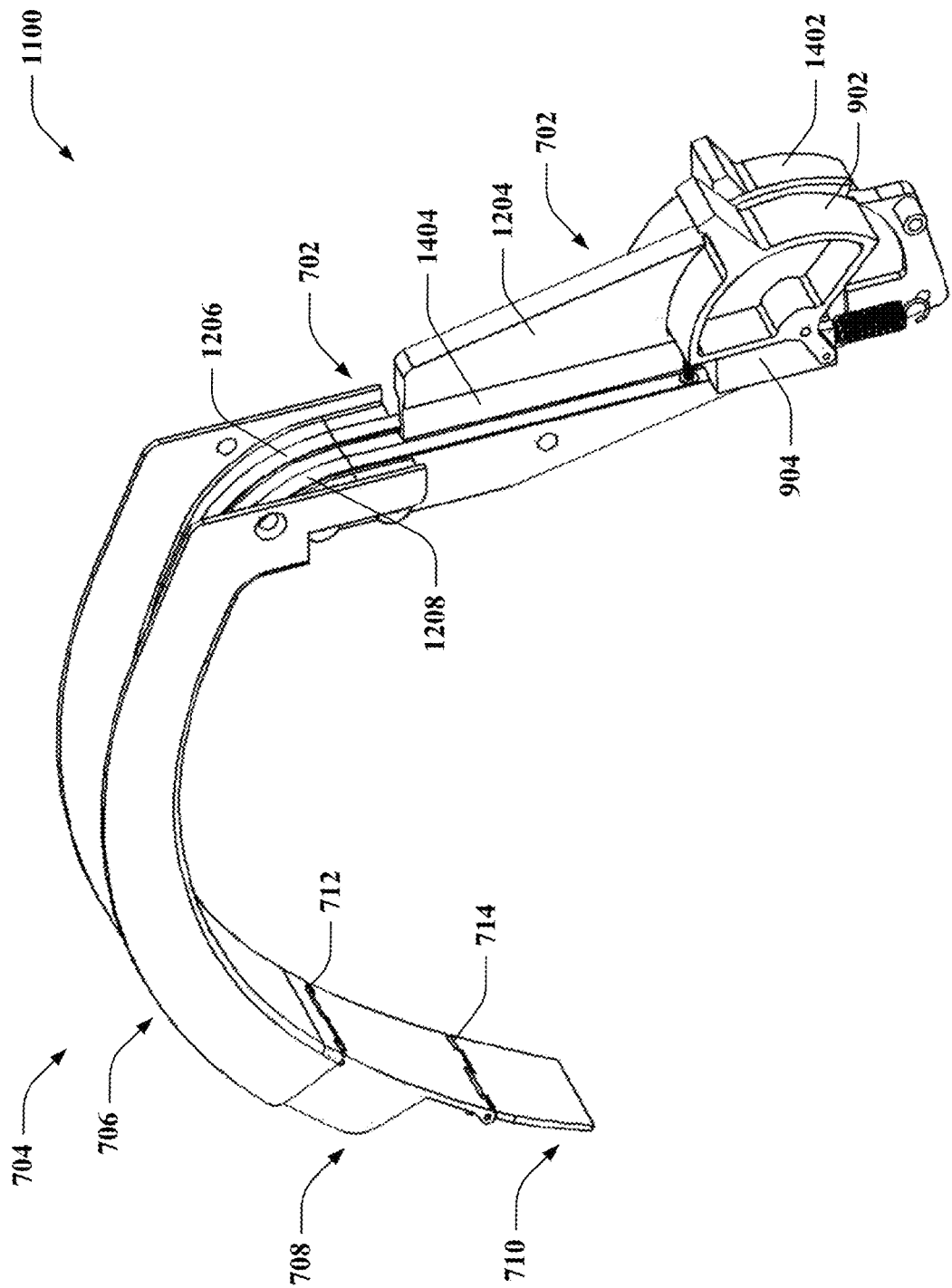

FIG. 14 illustrates another isometric view of the dynamic articulating laryngoscope 1100. As shown, the handle assembly 702 can include the knob 902, which can control manipulation of the blade assembly 704 at the fine control articulation point 714 (e.g., by moving the distal pusher 1208, . . . ), and a disparate knob 1402, which can control manipulation of the blade assembly 704 at the medium control articulation point 712 (e.g., by moving the proximal pusher 1206, . . . ).

Moreover, the handle chassis 1204 includes a channel 1404. The lever block 904 can move within the channel 1404 (e.g., the lever block 904 can be slidable within the channel 1404, . . . ) as controlled by the knob 902. Further, it is contemplated that a channel block (e.g., the channel block 906 of FIG. 9, . . . ) can be positioned at a top of the channel 1404 (e.g., near the blade assembly 704, . . . ) to stop movement of the lever block 904.

Figure 15:
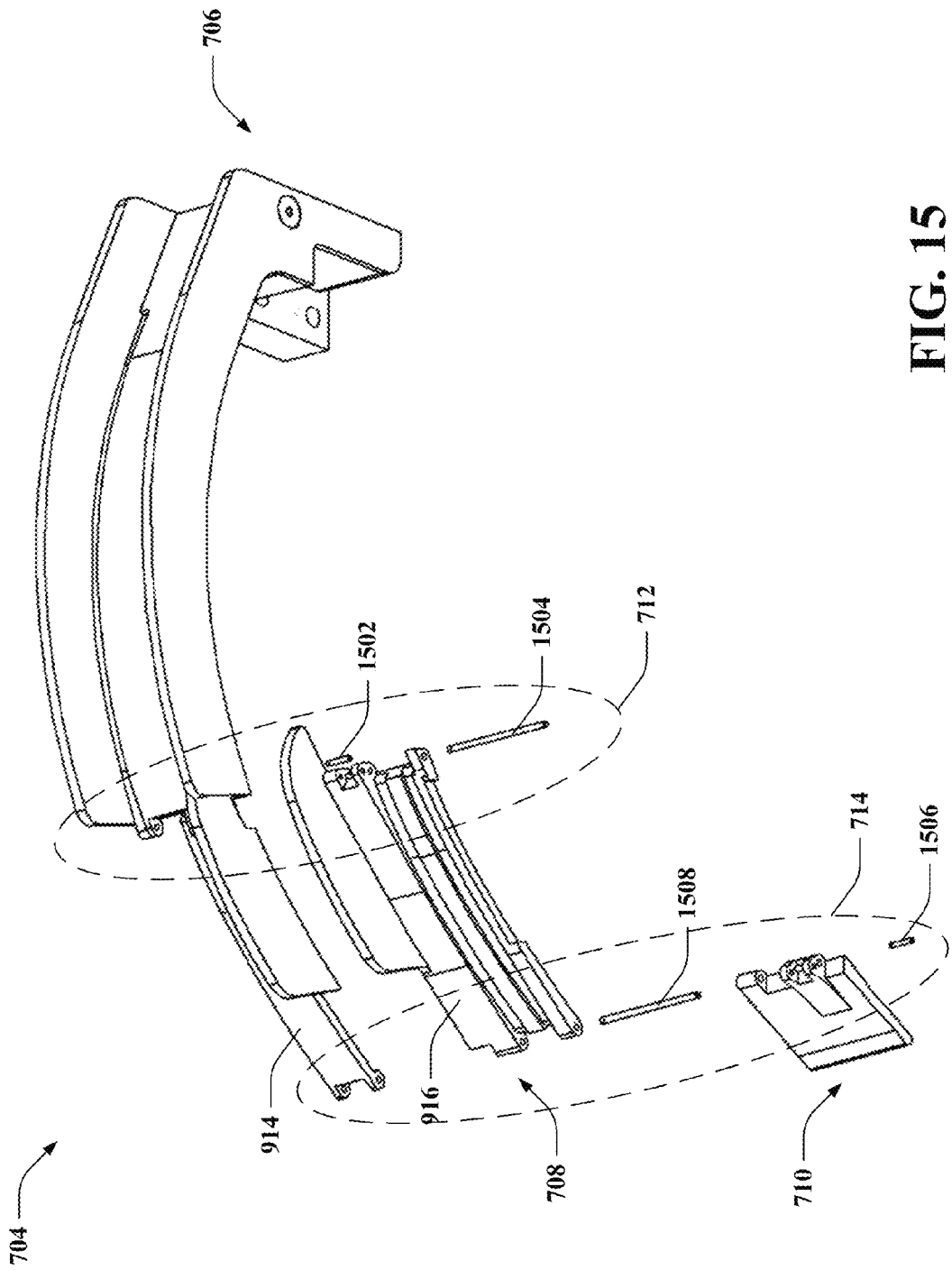
FIG. 15 illustrates an isometric view of the blade assembly.

Now turning to FIG. 15, illustrated is an isometric view of the blade assembly 704. The main blade assembly 706, the proximal blade assembly 708, and the distal blade assembly 710 are shown separated from each other. Moreover, FIG. 15 illustrates the medium control articulation point 712 and the fine control articulation point 714.

The medium control articulation point 712 can include a plurality of pins: namely, a pin 1502 (e.g., the pin 1106 of FIG. 11, . . . ) and a pin 1504. For example, the pin 1502 can couple the rotating link 810 of FIG. 8 to the proximal blade assembly 708. According to another example, the pin 1502 can couple the proximal pusher 1206 to the proximal blade assembly 708. Moreover, the pin 1504 can couple the main blade assembly 706 to the proximal blade assembly 708. Further, the pin 1502 and the pin 1504 can be offset from each other. Thus, manipulation of the rotating link 810 or the proximal pusher 1206 as described herein can yield a force upon the pin 1502, which can cause the proximal blade assembly 708 to rotate relative to the main blade assembly 706 about the pin 1504.

Further, the fine control articulation point 714 can include a plurality of pins: namely, a pin 1506 (e.g., the pin 1004 of FIG. 10, the pin 1108 of FIG. 11, . . . ) and a pin 1508. The pin 1506 can couple the pusher 908 of FIG. 9 (e.g., the distal pusher 1208 of FIG. 12, . . . ) to the distal blade assembly 710. Moreover, the pin 1508 can couple the proximal blade assembly 708 to the distal blade assembly 710. Further, the pin 1506 and the pin 1508 can be offset from each other. Accordingly, manipulation of the pusher 908 (e.g., the distal pusher 1208, . . . ) as described herein can yield a force upon the pin 1506, which can cause the distal blade assembly 710 to rotate relative to the proximal blade assembly 708 about the pin 1508.

Figure 16:
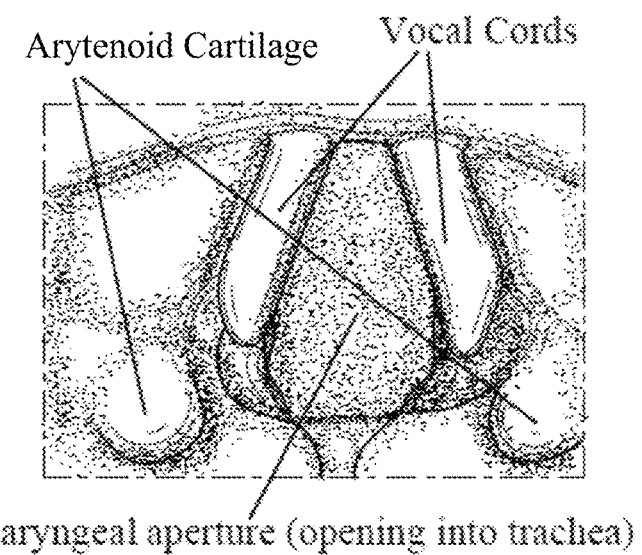
FIGS. 16 and 17 illustrate the vocal cords and laryngeal aperture.
Figure 17:
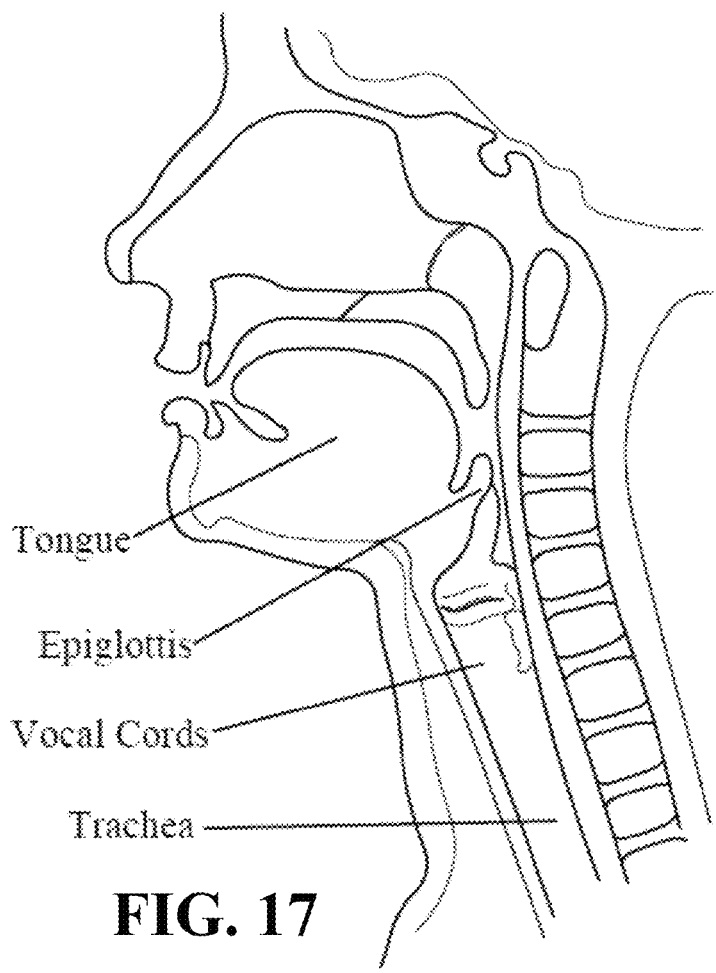
Figure 18:
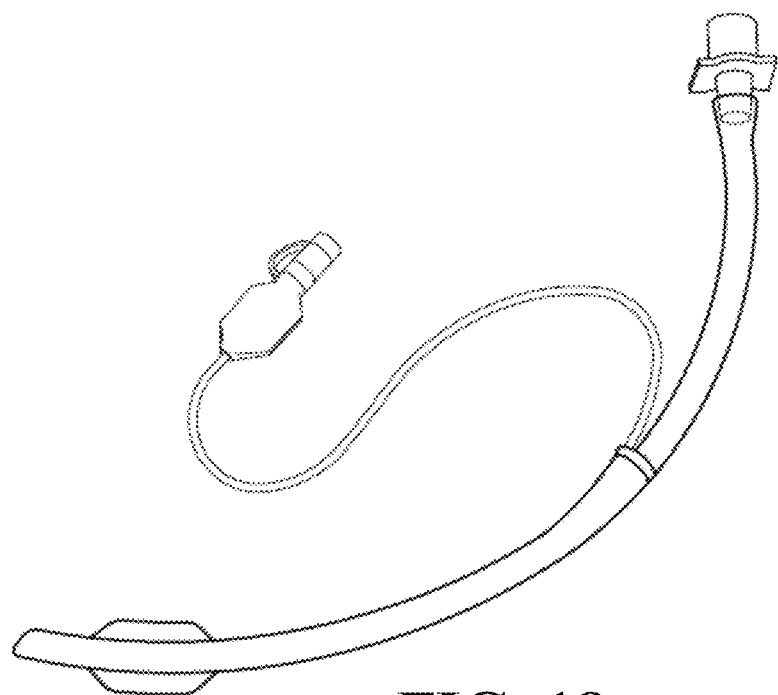
FIG. 18 illustrates an example endotracheal tube that can be utilized in connection with the airway management apparatus described herein.
Figure 19:
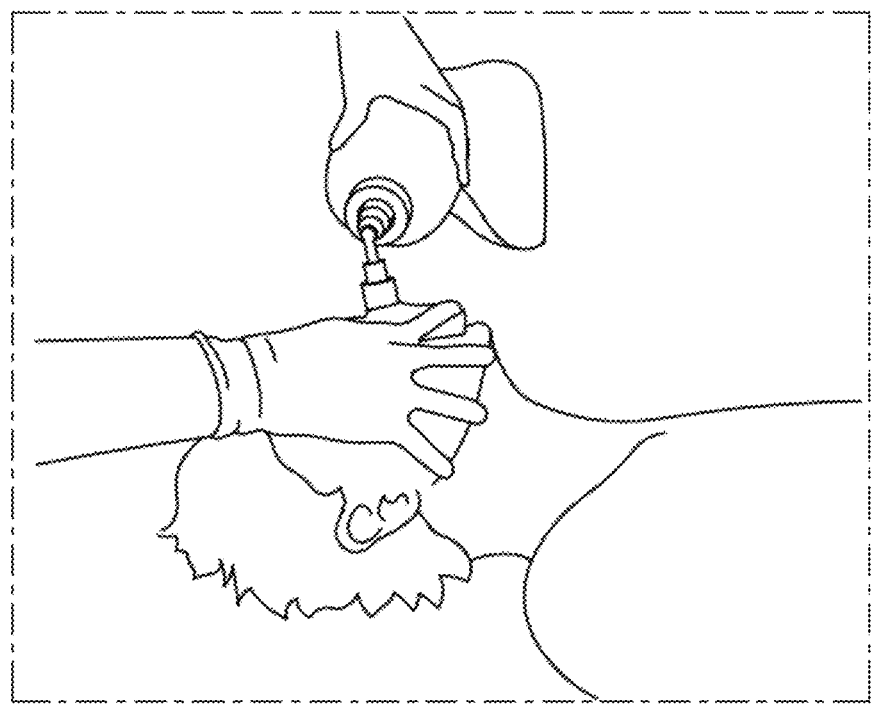
FIG. 19 illustrates bag-mask ventilation.

FIGS. 16 and 17 depict the vocal cords and laryngeal aperture. FIG. 18 illustrates an example endotracheal tube that can be utilized in connection with the airway management apparatus described herein. FIG. 19 illustrates bag-mask ventilation.

A typical example operating room intubation scenario proceeds as follows. A patient who is spontaneously breathing on their own is placed in a supine position and supplemental oxygen is provided in an attempt to "fill" their lungs, blood, and tissues with higher than normal oxygen levels, hyperoxygenation. This is done to prevent a fall in oxygen levels, deaturation or the oxygen carrying molecules hemoglobin in the blood, during the period when the patient is not breathing as a result of the administration of anesthetic drugs that render patients unconscious and apneic (not breathing on their own) and the initiation of mechanical ventilation through the properly placed endotracheal tube. Typically, with hyperoxygenation, an anesthesiologist has about 2-3 minutes to place the endotracheal tube into the trachea before the patient becomes hypoxic requiring the addition of supplemental oxygen delivered with bag-mask ventilation (as shown in FIG. 19). In certain situations, a failure to place the endotracheal tube into the trachea and start mechanical ventilation, bag-mask ventilation is extremely difficult or not possible resulting in severe hypoxia and potentially death or irreversible brain damage. These delays in securing an airway with the proper placement of an endotracheal tube extend the amount and time of anesthesia and add potential physiologic derangements that are poorly tolerated in certain patient populations, especially the elderly.

Complications with placement of an endotracheal tube do not end with visualization of the opening to the trachea. Placement of a rigid laryngoscope into someone's mouth and using this to forcefully move the tongue, lower jaw, and upper airway soft tissue out of the way is very stimulation and not reliably blunted with standard anesthetic induction medications. Endotracheal intubation can result in severe physiologic stresses in patient's that often lead to increases in heart rate and blood pressure in the adult population, and a precipitous fall in heart rate in pediatric patients. These stresses are not well tolerated in certain patient groups with co-existing heart conditions or those already at physiologic extremes (such as trauma patients).

If one starts with a patient who is spontaneously breathing and oxygenating themselves, which pertains to the majority of patients taken to the operating room for elective procedures, it is assumed they will be amenable to the placement of an endotracheal tube once anesthesia is administered, provided a comprehensive airway evaluation does not uncover any potential problems. Once anesthesia is administered, a once patent airway can become compromised by a relaxation of the upper airway musculature resulting in an obstruction that can be very difficult to overcome with bag-mask ventilation or the use of other airway devices. In these patients, a once patent airway when they were awake can now require immediate placement of an endotracheal tube into a trachea that is remote to the anesthesiologist. As described herein, the development of endoscopic equipment including small, high resolution cameras and the ability to digitalize and transmit an image has the potential to improve the viewing of the laryngeal aperture resulting in an easier, quicker, less traumatic and with reduced physiologic perturbations in patients undergoing general anesthetic as well as those requiring intubation for some other emergency medical condition elsewhere inside or outside the hospital. To date, typical devices have been unable to overcome the problems encountered in conventional laryngoscopy and intubation.

Various types of endoscopic equipment are routinely being used in many areas of medicine and surgery. These devices can be ridged or flexible and typically consist of a system to deliver a high intensity light beam to the area to be visualized. This light delivery is usually in the form of a fiberoptic cable. Most of these devices also use an external cable to connect the endoscopic device to some external power/light generating source by an additional cable. The camera at the tip of the endoscopic device can consist of a CCD (charge coupled device) sensor, in the form of a light sensitive chip that converts an optical source into an electrical one, or an array of fiberoptic cables coherently aligned to deliver the light encoded image back to some video display system through an external cable connection.

The ubiquitous use of endoscopic equipment in the health care system today has resulted in some sophisticated equipment; however, the series of interconnected cables makes these devices difficult to maneuver in the best situations, severely complicating and emergency situation or a procedure performed outside a well controlled environment. In addition, the fragility of fiberoptic bundles results in frequent and easy damage of these cables adding to the escalating health care costs. Relatively minimal damage to the fiberoptic bundles leads to a degradation in image quality that is unusable for the delicate medical procedures the endoscope was designed for.

In light of all of these problems, it is desirable to provide a video laryngoscopic system that is easy to use, adaptable to the wide variation in normal and abnormal upper airway pathology we see every day in the hospital, facilitates easy placement into a patients oral cavity with little or no stimulation, and allows for the transmission of a digital image to any number of video monitoring systems using wireless technology in place of external cable connections.

The ability to easily articulate a laryngoscopic blade that has already been placed into someone's oral cavity allows for utilizing a single device across a wide spectrum of normal and abnormal anatomic situations. Coupled with an articulating blade, a coherently adapting channel to guide the endotracheal tube to the exact position where the camera is looking is required to place the endotracheal tube and not just visualize where it needs to go.

In certain airway situations, the placement of an endotracheal can only safely be accomplished by keeping a patient in an awake state and spontaneously breathing. In these situations, is it of paramount importance that one is able to adequately anesthetize the upper airway to blunt the cough reflex as well as to blunt any painful stimuli these patients would experience with the placement of the intubation equipment. A single airway device that takes all of these situations into account would decrease the time required for intubation, decrease the stress on the patient, and reduce the cost of equipment as well as equipment processing time and expense.

The aforementioned objectives can be achieved with a completely redesigned laryngoscopic blade, an integrated digital stereoscopic camera and high intensity, low power light source and light conducting system, the addition of a liquid, atomizing device for the delivery of local anesthetic or humidification to the airway mucosa, a specialized, dynamically sizing channel that adapts to the contour of the laryngoscopic blade allowing for the delivery of an endotracheal tube or other airway device to the exact position of the camera view.

Figure 20:
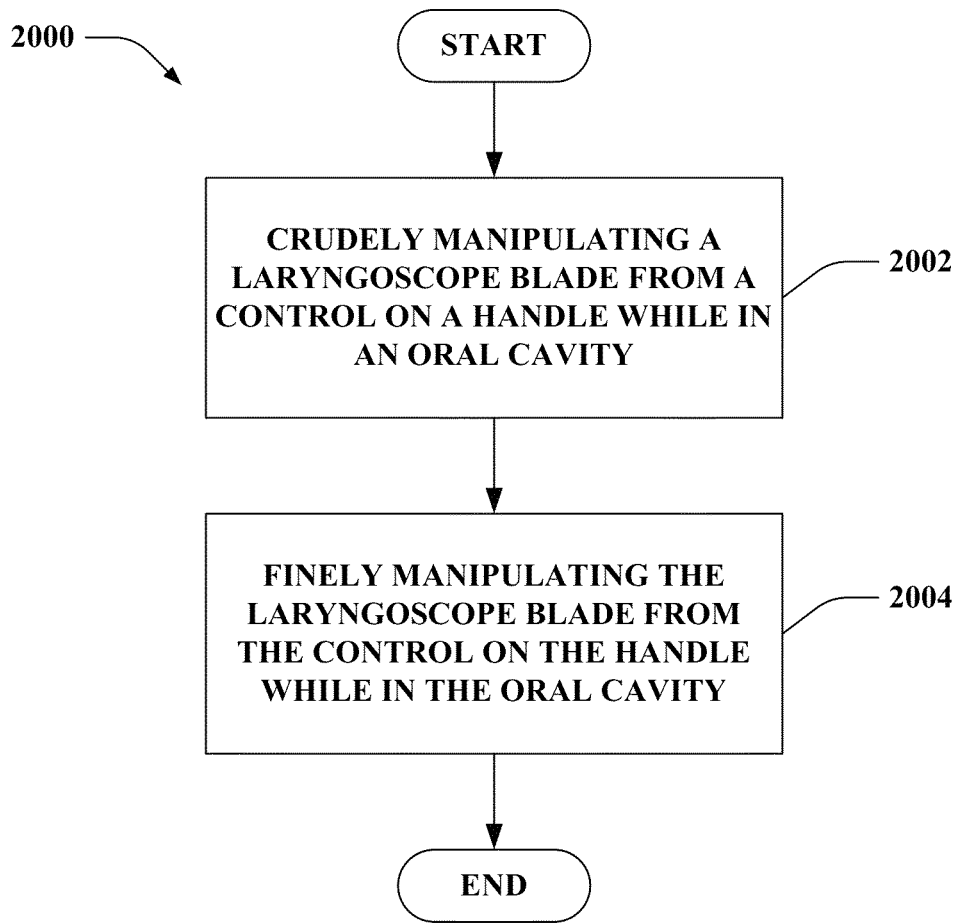
FIG. 20 illustrates an exemplary methodology that enables utilizing a laryngoscope with an articulating blade.
Figure 21:
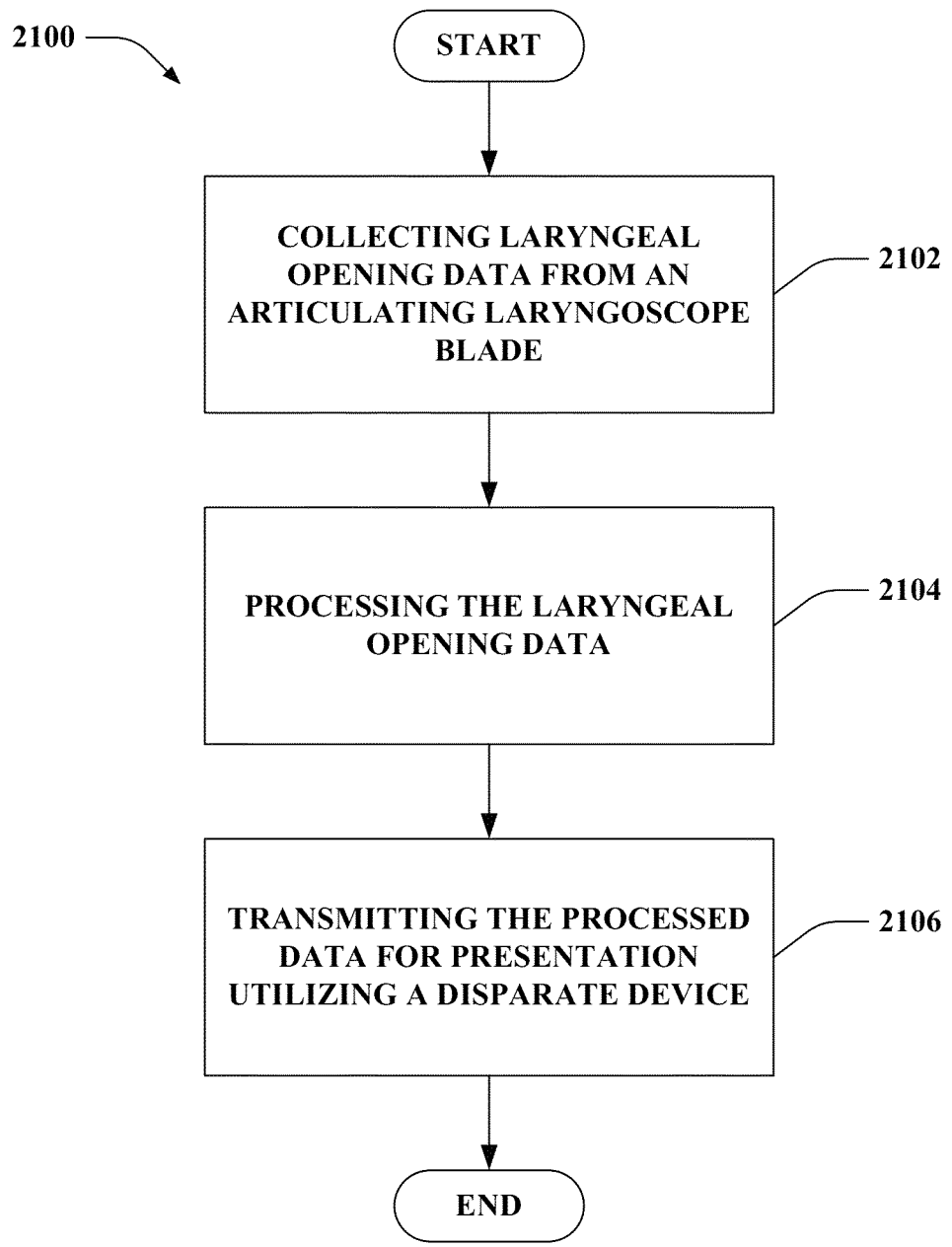
FIG. 21 illustrates an exemplary methodology that facilitates presenting data related to intubation upon an external device in real time.
Figure 22:
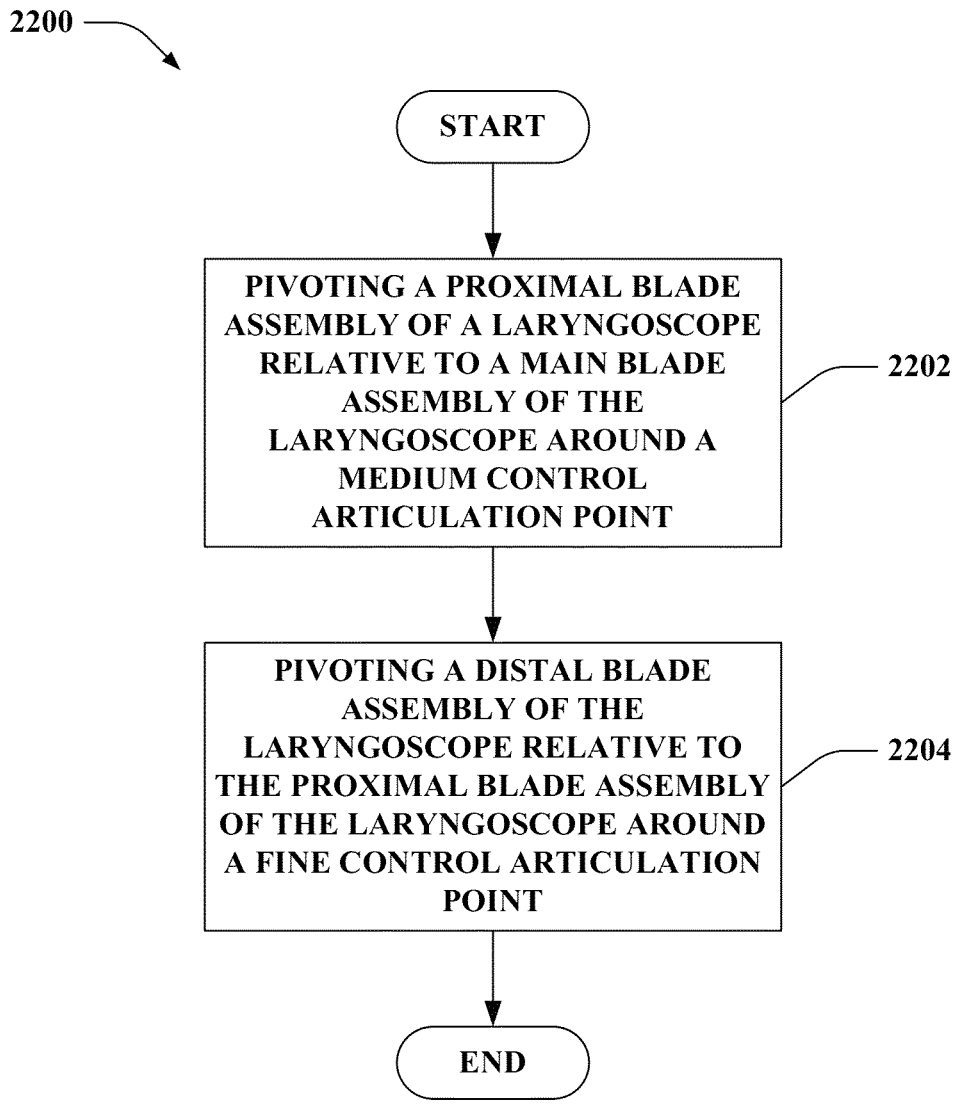
FIG. 22 illustrates an exemplary methodology that facilitates employing a laryngoscope (e.g., a dynamic articulating laryngoscope, . . . ).

FIGS. 20-22 illustrate methodologies in accordance with the claimed subject matter. For simplicity of explanation, the methodologies are depicted and described as a series of acts. It is to be understood and appreciated that the subject innovation is not limited by the acts illustrated and/or by the order of acts, for example acts can occur in various orders and/or concurrently, and with other acts not presented and described herein. Furthermore, not all illustrated acts may be required to implement the methodologies in accordance with the claimed subject matter. In addition, those skilled in the art will understand and appreciate that the methodologies could alternatively be represented as a series of interrelated states via a state diagram or events.

Referring to FIG. 20, illustrated is a methodology 2000 that enables utilizing a laryngoscope with an articulating blade. At 2002, a laryngoscope blade can be crudely manipulated from a control on a handle while in an oral cavity. The laryngoscope blade can be articulated to position one or more cameras included with the laryngoscope blade (e.g., incorporated into the blade, mounted upon the blade, . . . ) at the base of the tongue looking upwards towards the vocal cords. In contrast to conventional techniques where manipulation of the blade is conducted while outside of the oral cavity, manipulation of the laryngoscope blade can occur within the oral cavity in connection with the claimed subject matter; thus, repeated removal and reinsertion of the blade can be mitigated. At 2004, the laryngoscope blade can be finely manipulated from the control on the handle while in the oral cavity. The fine articulation, for example, can enable moving a tip of the blade to move the epiglottis, thereby yielding a clearer view of the vocal cords. It is contemplated that the crude and fine manipulation of the laryngoscope blade can be effectuated mechanically, via an electric signal, and so forth.

Turning to FIG. 21, illustrated is a methodology 2100 that facilitates presenting data related to intubation upon an external device in real time. At 2102, laryngeal opening data can be collected from an articulating laryngoscope blade. For example, data can be obtained utilizing digital cameras mounted upon and/or incorporated into the articulating laryngoscope blade. Further, the blade can be maneuvered to position the cameras with a clear view to the vocal cords. At 2104, the laryngeal opening data can be processed. For instance, data from a plurality of digital cameras can be combined to yield a stereoscopic view of the vocal cords. At 2106, the processed data can be transmitted for presentation utilizing a disparate device. The data can be transmitted wirelessly, for instance. Moreover, the processed data can be transferred to any type of disparate device that can yield an output. Thus, for example, the processed data can be sent wirelessly to a monitor in an operating room, a cell phone, a PDA, etc. Further, the disparate device can render an output in real time. Accordingly, as the laryngoscope blade is articulated within the oral cavity, a display can be rendered upon the disparate device in real time that shows a view of the vocal cords from the base of the tongue.

Referring to FIG. 22, illustrated is a methodology 2200 that facilitates employing a laryngoscope (e.g., a dynamic articulating laryngoscope, . . . ). At 2202, a proximal blade assembly of a laryngoscope can be pivoted relative to a main blade assembly of the laryngoscope around a medium control articulation point. For example, the proximal blade assembly can be pivoted while at least a portion of a blade assembly, which includes the main blade assembly, the proximal blade assembly, and a distal blade assembly, is positioned in an oral cavity; however, the claimed subject matter is not so limited. Further, the proximal blade assembly can be pivoted based upon a first input obtained at a handle assembly of the laryngoscope. By way of illustration, the first input can be obtained by a knob, button, joystick, switch, dial, lever, touch screen, voice command, sensor, mouse, trigger, or the like.

At 2204, a distal blade assembly of the laryngoscope can be pivoted relative to the proximal blade assembly of the laryngoscope around a fine control articulation point. For example, the distal blade assembly can be pivoted while at least a portion of the blade assembly is positioned in the oral cavity; however, the claimed subject matter is not so limited. Moreover, the distal blade assembly can be pivoted based upon a second input obtained at the handle assembly of the laryngoscope. By way of illustration, the second input can be obtained by a knob, button, joystick, switch, dial, lever, touch screen, voice command, sensor, mouse, trigger, or the like.

According to an example, the first input can cause a motor included in the handle assembly to drive a flexible shaft, which can rotate a lead screw. Rotation of the lead screw can be translated into linear motion of a sliding link, which can cause a rotating link to pivot the proximal blade assembly relative to the main blade assembly around the medium control articulation point. By way of another example, the first input can cause a lever block to move within a channel formed as part of a handle chassis included as part of the handle assembly. Further, movement of the lever block can cause a proximal pusher, which is attached to the lever block and the proximal blade assembly, to slide within a channel formed between blade covers and blades of the blade assembly. Sliding of the proximal pusher can pivot the proximal blade assembly relative to the main blade assembly around the medium control articulation point.

Moreover, the second input can cause a lever block to move within a channel formed as part of a handle chassis included as part of the handle assembly. Further, movement of the lever block can cause a distal pusher, which is attached to the lever block and the distal blade assembly, to slide within a channel formed between blade covers and blades of the blade assembly. Sliding of the distal pusher can pivot the distal blade assembly relative to the proximal blade assembly around the fine control articulation point.

Figure 23:
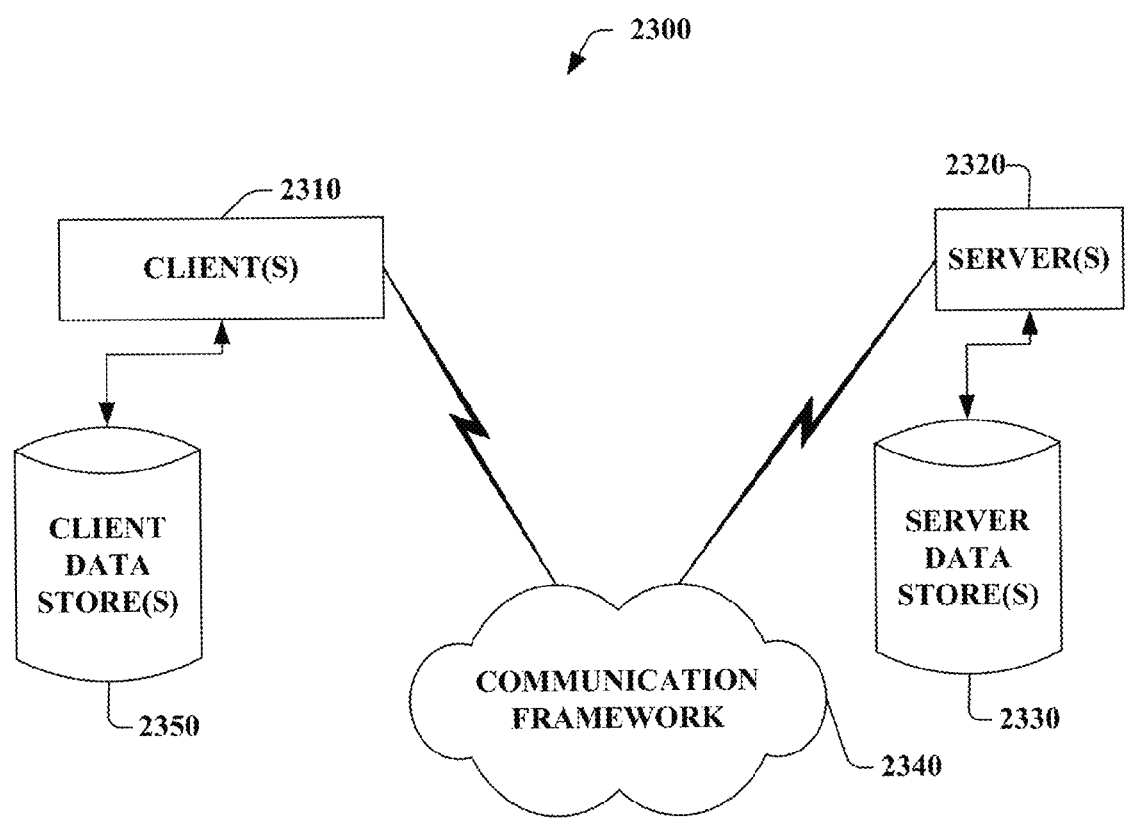
FIG. 23 illustrates an exemplary networking environment, wherein the novel aspects of the claimed subject matter can be employed.
Figure 24:
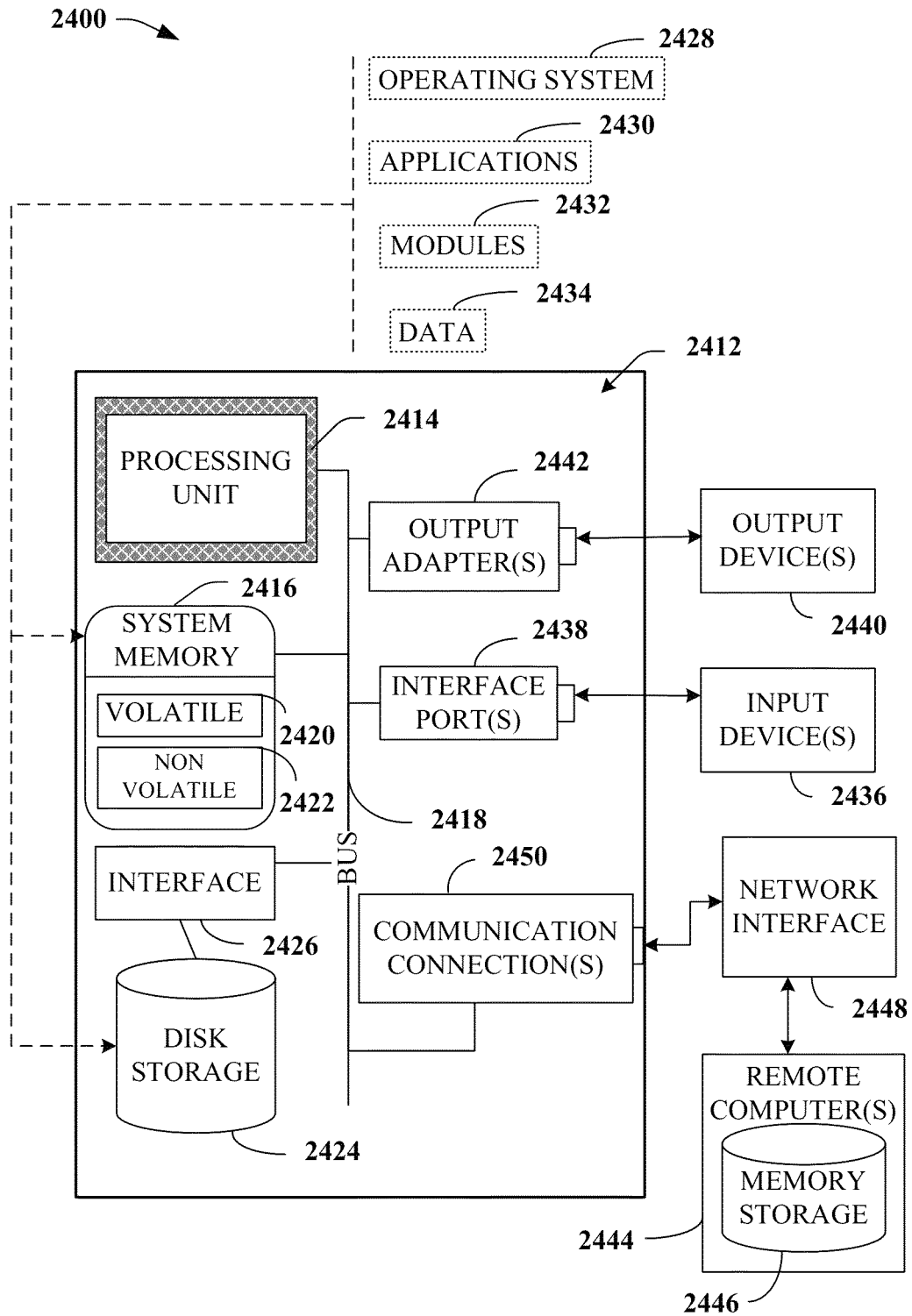
FIG. 24 illustrates an exemplary operating environment that can be employed in accordance with the claimed subject matter.

In order to provide additional context for implementing various aspects of the claimed subject matter, FIGS. 23-24 and the following discussion is intended to provide a brief, general description of a suitable computing environment in which the various aspects of the subject innovation may be implemented. For instance, FIGS. 23-24 set forth a suitable computing environment that can be employed in connection with generating and/or utilizing replicas of states. While the claimed subject matter has been described above in the general context of computer-executable instructions of a computer program that runs on a local computer and/or remote computer, those skilled in the art will recognize that the subject innovation also may be implemented in combination with other program modules. Generally, program modules include routines, programs, components, data structures, etc., that perform particular tasks and/or implement particular abstract data types.

Moreover, those skilled in the art will appreciate that the inventive methods may be practiced with other computer system configurations, including single-processor or multi-processor computer systems, minicomputers, mainframe computers, as well as personal computers, hand-held computing devices, microprocessor-based and/or programmable consumer electronics, and the like, each of which may operatively communicate with one or more associated devices. The illustrated aspects of the claimed subject matter may also be practiced in distributed computing environments where certain tasks are performed by remote processing devices that are linked through a communications network. However, some, if not all, aspects of the subject innovation may be practiced on stand-alone computers. In a distributed computing environment, program modules may be located in local and/or remote memory storage devices.

FIG. 23 is a schematic block diagram of a sample-computing environment 2300 with which the claimed subject matter can interact. The system 2300 includes one or more client(s) 2310. The client(s) 2310 can be hardware and/or software (e.g., threads, processes, computing devices). The system 2300 also includes one or more server(s) 2320. The server(s) 2320 can be hardware and/or software (e.g., threads, processes, computing devices). The servers 2320 can house threads to perform transformations by employing the subject innovation, for example.

One possible communication between a client 2310 and a server 2320 can be in the form of a data packet adapted to be transmitted between two or more computer processes. The system 2300 includes a communication framework 2340 that can be employed to facilitate communications between the client(s) 2310 and the server(s) 2320. The client(s) 2310 are operably connected to one or more client data store(s) 2350 that can be employed to store information local to the client(s) 2310. Similarly, the server(s) 2320 are operably connected to one or more server data store(s) 2330 that can be employed to store information local to the servers 2320.

With reference to FIG. 24, an exemplary environment 2400 for implementing various aspects of the claimed subject matter includes a computer 2412. The computer 2412 includes a processing unit 2414, a system memory 2416, and a system bus 2418. The system bus 2418 couples system components including, but not limited to, the system memory 2416 to the processing unit 2414. The processing unit 2414 can be any of various available processors. Dual microprocessors and other multiprocessor architectures also can be employed as the processing unit 2414.

The system bus 2418 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCM-CIA), Firewire (IEEE 1394), and Small Computer Systems Interface (SCSI).

The system memory 2416 includes volatile memory 2420 and nonvolatile memory 2422. The basic input/output system (BIOS), containing the basic routines to transfer information between elements within the computer 2412, such as during start-up, is stored in nonvolatile memory 2422. By way of illustration, and not limitation, nonvolatile memory 2422 can include read only memory (ROM), programmable ROM (PROM), electrically programmable ROM (EPROM), electrically erasable programmable ROM (EEPROM), or flash memory. Volatile memory 2420 includes random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), Rambus direct RAM (RDRAM), direct Rambus dynamic RAM (DRDRAM), and Rambus dynamic RAM (RDRAM).

Computer 2412 also includes removable/non-removable, volatile/non-volatile computer storage media. FIG. 24 illustrates, for example a disk storage 2424. Disk storage 2424 includes, but is not limited to, devices like a magnetic disk drive, floppy disk drive, tape drive, Jaz drive, Zip drive, LS-100 drive, flash memory card, or memory stick. In addition, disk storage 2424 can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage devices 2424 to the system bus 2418, a removable or non-removable interface is typically used such as interface 2426.

It is to be appreciated that FIG. 24 describes software that acts as an intermediary between users and the basic computer resources described in the suitable operating environment 2400. Such software includes an operating system 2428. Operating system 2428, which can be stored on disk storage 2424, acts to control and allocate resources of the computer system 2412. System applications 2430 take advantage of the management of resources by operating system 2428 through program modules 2432 and program data 2434 stored either in system memory 2416 or on disk storage 2424. It is to be appreciated that the claimed subject matter can be implemented with various operating systems or combinations of operating systems.

A user enters commands or information into the computer 2412 through input device(s) 2436. Input devices 2436 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 2414 through the system bus 2418 via interface port(s) 2438. Interface port(s) 2438 include, for example, a serial port, a parallel port, a game port, and a universal serial bus (USB). Output device(s) 2440 use some of the same type of ports as input device(s) 2436. Thus, for example, a USB port may be used to provide input to computer 2412, and to output information from computer 2412 to an output device 2440. Output adapter 2442 is provided to illustrate that there are some output devices 2440 like monitors, speakers, and printers, among other output devices 2440, which require special adapters. The output adapters 2442 include, by way of illustration and not limitation, video and sound cards that provide a means of connection between the output device 2440 and the system bus 2418. It should be noted that other devices and/or systems of devices provide both input and output capabilities such as remote computer(s) 2444.

Computer 2412 can operate in a networked environment using logical connections to one or more remote computers, such as remote computer(s) 2444. The remote computer(s) 2444 can be a personal computer, a server, a router, a network PC, a workstation, a microprocessor based appliance, a peer device or other common network node and the like, and typically includes many or all of the elements described relative to computer 2412. For purposes of brevity, only a memory storage device 2446 is illustrated with remote computer(s) 2444. Remote computer(s) 2444 is logically connected to computer 2412 through a network interface 2448 and then physically connected via communication connection 2450. Network interface 2448 encompasses wire and/or wireless communication networks such as local-area networks (LAN) and wide-area networks (WAN). LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 2450 refers to the hardware/software employed to connect the network interface 2448 to the bus 2418. While communication connection 2450 is shown for illustrative clarity inside computer 2412, it can also be external to computer 2412. The hardware/software necessary for connection to the network interface 2448 includes, for exemplary purposes only, internal and external technologies such as, modems including regular telephone grade modems, cable modems and DSL modems, ISDN adapters, and Ethernet cards.

What has been described above includes examples of the subject innovation. It is, of course, not possible to describe every conceivable combination of components or methodologies for purposes of describing the claimed subject matter, but one of ordinary skill in the art may recognize that many further combinations and permutations of the subject innovation are possible. Accordingly, the claimed subject matter is intended to embrace all such alterations, modifications, and variations that fall within the spirit and scope of the appended claims.

In particular and in regard to the various functions performed by the above described components, devices, circuits, systems and the like, the terms (including a reference to a "means") used to describe such components are intended to correspond, unless otherwise indicated, to any component which performs the specified function of the described component (e.g., a functional equivalent), even though not structurally equivalent to the disclosed structure, which performs the function in the herein illustrated exemplary aspects of the claimed subject matter. In this regard, it will also be recognized that the innovation includes a system as well as a computer-readable medium having computer-executable instructions for performing the acts and/or events of the various methods of the claimed subject matter.

In addition, while a particular feature of the subject innovation may have been disclosed with respect to only one of several implementations, such feature may be combined with one or more other features of the other implementations as may be desired and advantageous for any given or particular application. Furthermore, to the extent that the terms "includes," and "including" and variants thereof are used in either the detailed description or the claims, these terms are intended to be inclusive in a manner similar to the term "comprising."

What is claimed is:

1. An airway management apparatus, comprising:
    a blade portion operatively attached to a handle portion;
    the blade portion comprises a first flat blade comprising a first end attached to the handle portion, and a second end attached to a first end of a second flat blade at a first articulation point, the second flat blade comprising a second end attached to a first end of a third flat blade at a second articulation point, wherein the second flat blade is movable relative to the first articulation point between a first and second position and the third flat blade is movable relative to the second articulation point between an open position and a flex position; and
    the handle portion comprises a first control configured to manipulate the blade portion at the first articulation point and a second control configured to manipulate the blade portion at the second articulation point, wherein a movement of the blade portion at the first articulation point is independent of another movement of the blade portion at the second articulation point.

2. The airway management apparatus of claim 1, wherein the first control and the second control are further configured to flex the blade portion through a length of the blade portion.

3. The airway management apparatus of claim 1, wherein the first control and the second control are configured to independently alter a curvature, an orientation, a size, a shape, or combinations thereof, of the blade portion.

4. The airway management apparatus of claim 1, wherein the first control is configured to rotate the second flat blade about the first articulation point and the second control is configured to rotate the third flat blade about the second articulation point.

5. The airway management apparatus of claim 1, wherein the handle portion further comprises a blade control component configured to receive an input that provides an instruction to the first control, the second control, or both the first control and the second control.

6. The airway management apparatus of claim 5, wherein the input is received from a device located remote from the airway management apparatus.

7. The airway management apparatus of claim 1, wherein the handle portion comprises:
    at least one knob configured to operate at least one of the first control or the second control;
    a lever block coupled to the at least one knob; and
    a handle chassis comprising a channel and a channel block, wherein the lever block is configured to move within the channel and the channel block is configured to limit a range of motion of the lever block within the channel.

8. The airway management apparatus of claim 7, wherein the channel block is configured to limit the range of motion of the lever block in a direction towards the blade portion.

9. The airway management apparatus of claim 7, the at least one knob is a rotatable knob and the lever block is configured to slide within the channel as a result of rotation of the rotatable knob and rotate at least one of the second flat blade about the first articulation point or the third flat blade about the second articulation point.

10. The airway management apparatus of claim 1, the handle portion being selectively removable from the blade portion.

11. The airway management apparatus of claim 1, further comprising a camera operatively attached to the blade portion, wherein the camera moves independently from the blade portion.

12. A laryngoscope, comprising:
    a handle assembly; and
    a blade assembly operatively attached to the handle assembly, the blade assembly comprises:
        a first blade assembly comprising a first blade cover and a first blade;
        a second blade assembly operatively connected to the first blade assembly at a first articulation point and movable through a proximal blade assembly range of motion, the second blade assembly comprises a second blade cover and a second blade; and
        a third blade assembly operatively connected to the second blade assembly at a second articulation point and movable through a distal blade assembly range of motion that is separate from the second blade assembly range of motion.

13. The laryngoscope of claim 12, the first blade assembly further comprising first blade flanges and the second blade assembly further comprising second blade flanges, wherein the first blade flanges and the second blade flanges are configured as sidewalls that form an adaptable channel.

14. The laryngoscope of claim 12, further comprising:
    a first pusher configured to move the second blade assembly about the first articulation point; and a second pusher configured to move the third blade assembly about the second articulation point.

15. The laryngoscope of claim 14, wherein the handle assembly comprises a first blade control component configured to operate the first pusher and a second blade control component configured to operate the second pusher.

16. The laryngoscope of claim 14, further comprising at least one camera operatively attached to the blade assembly.

17. The laryngoscope of claim 12, the handle assembly being selectively removable from the blade assembly.

18. The laryngoscope of claim 12, the handle assembly comprises a blade control component configured to receive a signal that comprises an instruction to move one or more of the first blade assembly, the second blade assembly, or the third blade assembly, wherein the signal is received from a device located remote from the laryngoscope.

19. A method, comprising:
   sending a first image to a first device, wherein the first image is captured by a camera operatively attached and configured to move independently of a laryngoscope comprising a first blade and a second blade;
   receiving a first input from the first device, the first input comprises a first instruction to move the first blade relative to a first articulation point;
   moving the first blade at the first articulation point;
   transmitting a second image to the first device, wherein the second image is captured by the camera or by another camera operatively attached and configured to move independently of the laryngoscope;
   receiving a second input from the first device, the second input comprises a second instruction to move the first blade relative to the first articulation point and through a first range of motion, or an instruction to move the second blade relative to a second articulation point and through a second range of motion that is separate from the first range of motion; and
   moving the first blade at the first articulation point or the second blade at the second articulation point, wherein the laryngoscope is at a first location and the first device is at a second location.

20. The method of claim 19, wherein the moving the first blade at the first articulation point or the second blade at the second articulation point comprises activating at least one motor operatively attached to the laryngoscope.

* * * * *